(12) United States Patent
Klosterman et al.

(10) Patent No.: US 7,114,368 B2
(45) Date of Patent: Oct. 3, 2006

(54) APPARATUS AND METHOD FOR VERIFYING THE VOLUME OF LIQUID DISPENSED BY A LIQUID-DISPENSING MECHANISM

(75) Inventors: Kurt M. Klosterman, Gurnee, IL (US); Ganesh Rajagopal, Carrollton, TX (US); Larry R. Jibson, Mundelein, IL (US); James L. Dempski, Green Oaks, IL (US); Paul A. Matuszewski, Wauconda, IL (US); Jeffrey W. Stewart, Bedford, TX (US); Jeffrey R. Swanson, Waukegan, IL (US); David M. Tipotsch, Double Oak, TX (US); Randall E. Youngs, Bedford, TX (US); Noman A. Abunimeh, Grayslake, IL (US)

(73) Assignee: Abbott Laboratories, Abbott Park, IL (US)

( * ) Notice: Subject to any disclaimer, the term of this patent is extended or adjusted under 35 U.S.C. 154(b) by 87 days.

(21) Appl. No.: 10/409,282

(22) Filed: Apr. 8, 2003

(65) Prior Publication Data
US 2004/0200260 A1    Oct. 14, 2004

(51) Int. Cl.
*G01D 18/00*    (2006.01)
*G01F 25/00*    (2006.01)
*G01G 23/01*    (2006.01)

(52) U.S. Cl. .................... 73/1.88; 73/1.34; 73/1.36; 73/1.73; 73/1.74; 702/86; 702/87; 702/88; 702/102

(58) Field of Classification Search ........ 73/1.01–1.03, 73/1.13, 1.15, 1.34, 1.36, 1.73, 1.74, 1.88; 702/85–88, 100–102, 104, 105
See application file for complete search history.

(56) References Cited

U.S. PATENT DOCUMENTS

| | | | | |
|---|---|---|---|---|
| 4,061,198 A | * | 12/1977 | Caldicott | 177/50 |
| 4,491,248 A | * | 1/1985 | Blackwell | 222/249 |
| 4,705,126 A | * | 11/1987 | Naito | 177/50 |
| 4,848,478 A | * | 7/1989 | Hafner | 177/50 |
| 4,850,442 A | * | 7/1989 | Naito et al. | 177/164 |
| 5,120,199 A | | 6/1992 | Youngs et al. | |
| 5,156,194 A | * | 10/1992 | von Nehring et al. | 141/1 |
| 5,174,400 A | | 12/1992 | Hasegawa et al. | |

(Continued)

FOREIGN PATENT DOCUMENTS

EP    1 099 941    5/2001

OTHER PUBLICATIONS

Kester, Walt, "Analog Devices—Practical Design Techniques for Sensor Signal Conditioning", 1999, Analog Devices, Inc., pp. 1-25.*

(Continued)

*Primary Examiner*—Hezron Williams
*Assistant Examiner*—David A. Rogers
(74) *Attorney, Agent, or Firm*—David L. Weinstein

(57) ABSTRACT

An apparatus for improving the procedure for quantifying the volume of liquid dispensed by a liquid-dispensing mechanism of an analytical instrument. The apparatus of this invention comprises (a) at least one weigh cup; (b) at least one standard mass; (c) at least one transducer assembly to convert a value of weight to an electrical response; and (d) at least one electronic circuit for converting the electrical response to a measurement of volume. This invention provides a method for calibrating readings of the volume of liquid dispensed by a liquid-dispensing mechanism of an analytical instruments so that absolute measurements of the volume of liquid dispensed can be obtained.

4 Claims, 47 Drawing Sheets

U.S. PATENT DOCUMENTS

| | | | |
|---|---|---|---|
| 5,246,354 A | | 9/1993 | Pardinas |
| 5,299,446 A | | 4/1994 | Pardinas et al. |
| 5,463,895 A | | 11/1995 | Brentz |
| 5,559,339 A | | 9/1996 | Domanik et al. |
| 5,628,929 A | | 5/1997 | Klosterman |
| 5,640,334 A | * | 6/1997 | Freeman et al. ............ 702/101 |
| 5,644,492 A | * | 7/1997 | Reichmuth et al. ......... 705/415 |
| 5,959,219 A | | 9/1999 | Saunders |
| 6,220,312 B1 | * | 4/2001 | Hirsch et al. ................. 141/83 |
| 6,541,063 B1 | * | 4/2003 | Prentice et al. ................ 427/8 |
| 6,557,391 B1 | * | 5/2003 | Luchinger ................... 73/1.13 |
| 6,769,292 B1 | * | 8/2004 | Mansky et al. ............ 73/54.05 |
| 2003/0062095 A1 | * | 4/2003 | Berghoff et al. ............ 141/198 |
| 2004/0065485 A1 | * | 4/2004 | Kats et al. .............. 177/210 R |

OTHER PUBLICATIONS

View, Abbott Prism® from every perspective, Abbott PRISM The Proven Solution, Brochure (2000) Abbott Park, Illinois.

"Electric—Resistance Strain Gauge", The Way Things Work, vol. Two, Simon and Schuster (New York: 1971), 480-483.

Copy of the PCT Search Report, For PCT/US04/010534.

\* cited by examiner

| FIG.22-1 | FIG.22-2 | FIG.22-3 | FIG.22-4 |
|---|---|---|---|
| FIG.22-5 | FIG.22-6 | FIG.22-7 | FIG.22-8 |
| FIG.22-9 | FIG.22-10 | FIG.22-11 | FIG.22-12 |
| FIG.22-13 | FIG.22-14 | FIG.22-15 | |

FIG.22

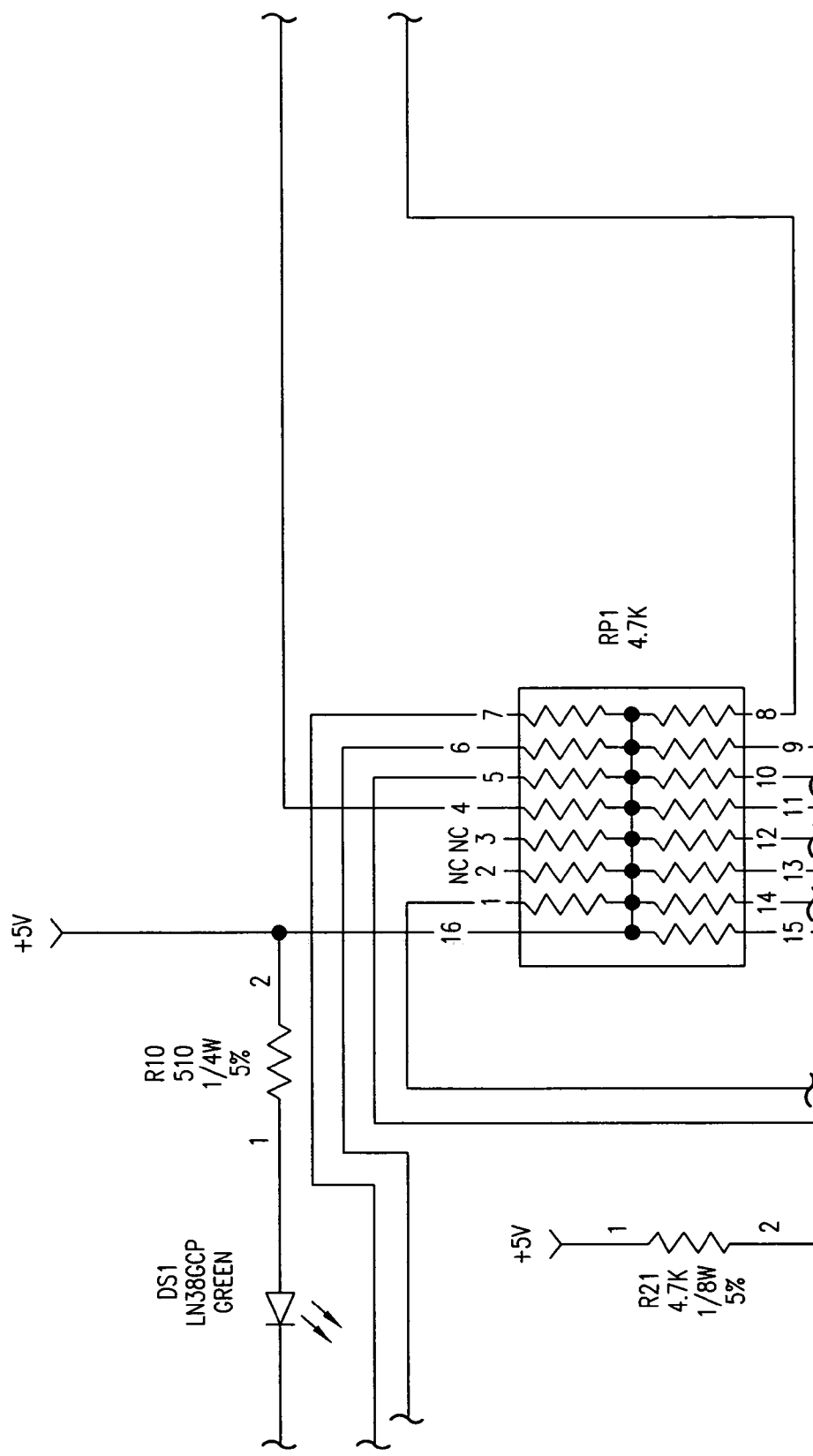

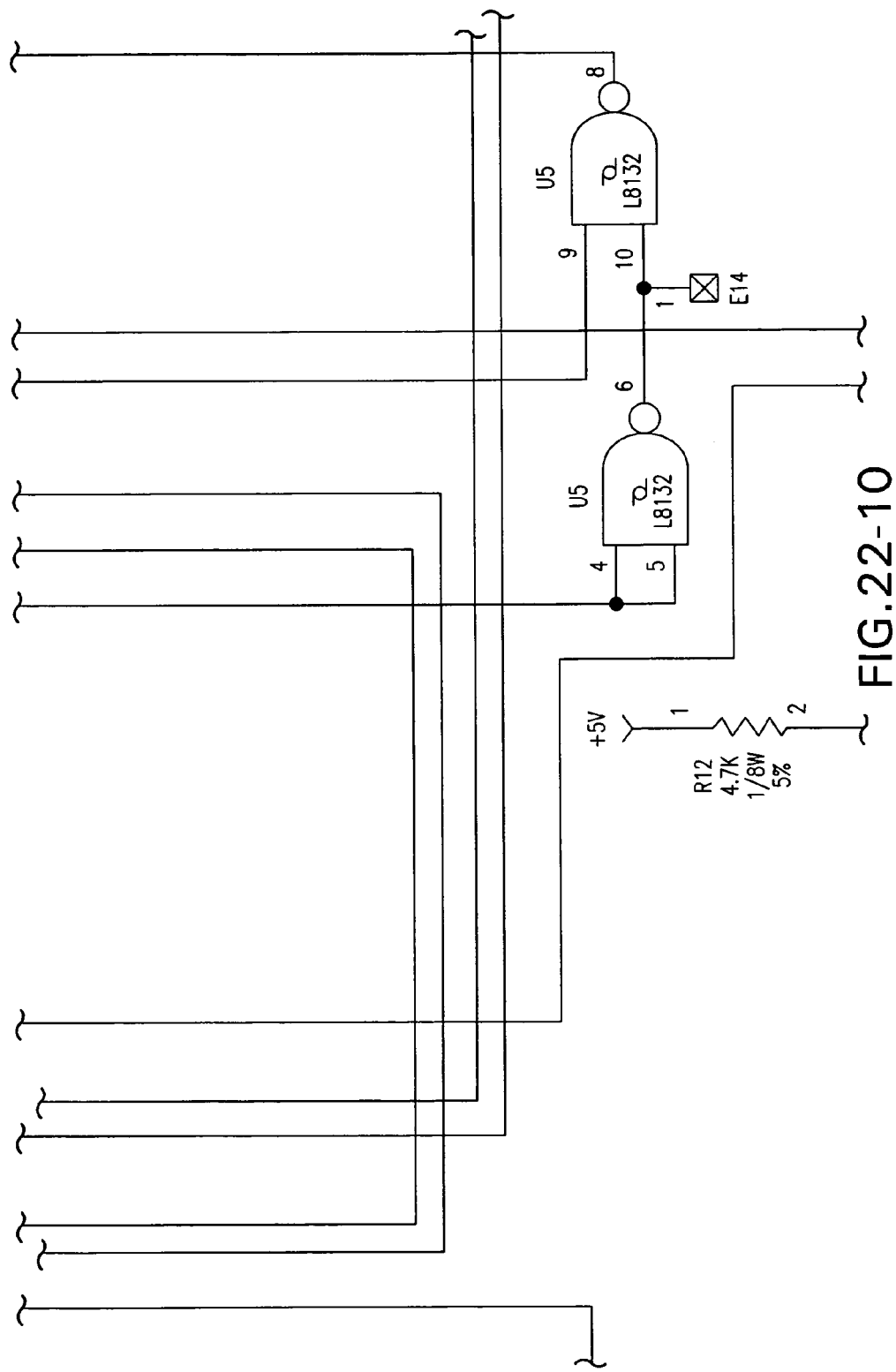

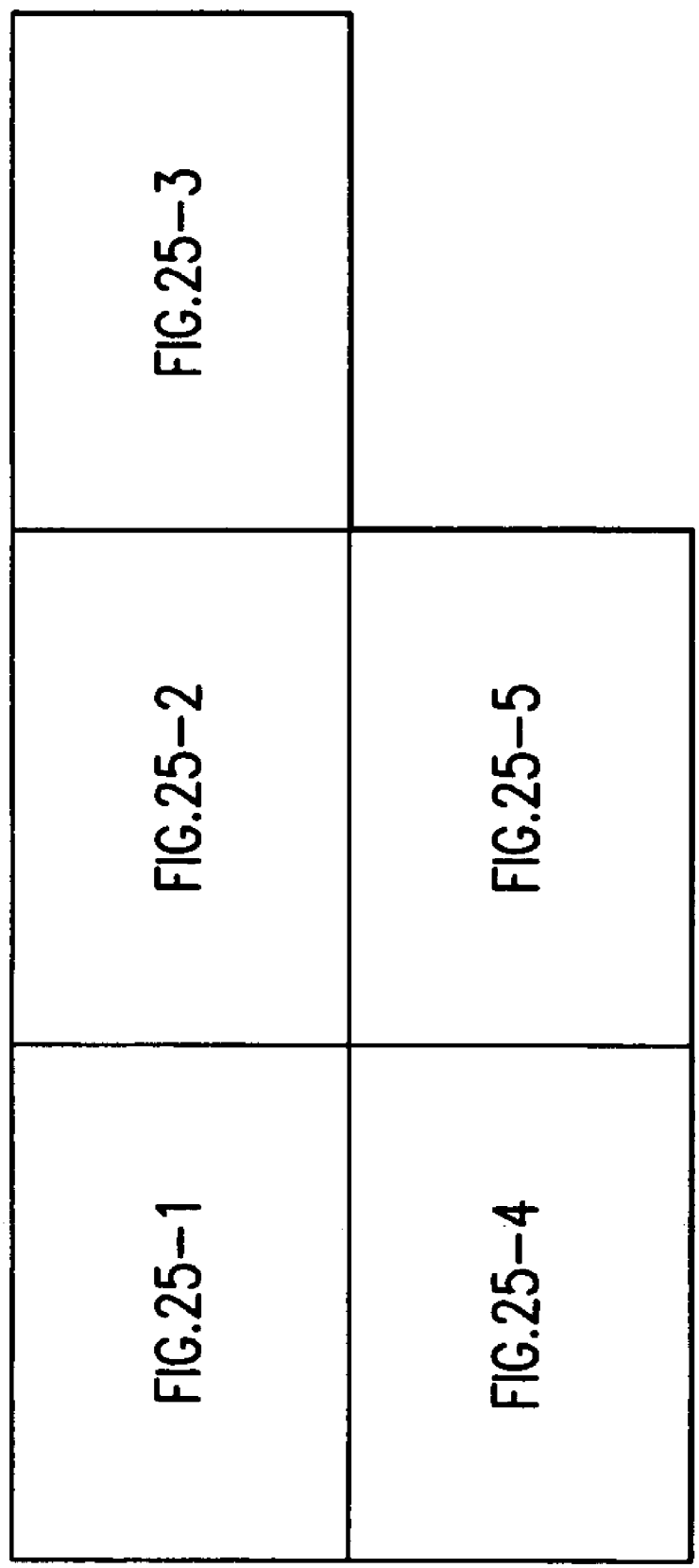

APPARATUS AND METHOD FOR VERIFYING THE VOLUME OF LIQUID DISPENSED BY A LIQUID-DISPENSING MECHANISM

BACKGROUND OF THE INVENTION

1. Field of the Invention

This invention relates to calibration of instruments for automated analysis of liquid samples.

2. Discussion of the Art

Increasing public awareness of the need for the safety of the blood supply for transfusions has caused the transfusion industry to move toward the use of automated instruments, increased scrutiny by regulatory agencies, and centralization of blood bank testing. The "ABBOTT PRISM" system was conceived as an automated, high-volume, blood banking virology instrument that would reduce the need for highly trained instrument operators. According to the "ABBOTT PRISM" system, after the instrument automatically scans the samples during the loading process, the operator follows a simple set of menu-driven commands to initiate sample runs. The system can process 160 samples, or up to 960 tests, per hour. The only intervention required of the operator, with the exception of loading the racks with samples to be tested, involves adding commodities (e.g., pipette tips, reaction trays) and emptying two containers that hold solid waste. The system informs the operator when further action is required to continue processing samples. At the end of a batch of sample runs, the system can automatically print requested reports that include all the necessary information relating to the batch of sample runs for the laboratory.

Occasionally, the "ABBOTT PRISM" system requires the replacement of a liquid-dispensing component that is no longer operational. After the component is replaced, one must independently verify that the volume of liquid dispensed by the component falls within a specified range. A volume verification tool is used during maintenance procedures to check volumes of several liquid-dispensing mechanisms for liquids, such as, for example, sample probes, metering pumps for liquids, and the like. The volume verification tool uses an indirect measurement of capacitance to determine the height of a liquid in a containment vessel in order to determine the volume of fluid in the vessel. This measurement technique is subject to the effects of surface tension on the walls of the containment vessel. The meniscus of the fluid dispensed does not always uniformly adhere to the walls of the containment vessel, thereby causing the volume verification tool to fail the requirements for making a reading of the measurement, and, consequently, delay the user in completing the system checks required to restore the "ABBOTT PRISM" system to normal operation.

Users often find the volume verification tool difficult to use, thereby resulting in delays. In some cases, the completion of this verification procedure may require up to three days. Performance of the volume verification procedure can be improved marginally by certain techniques. These techniques include:

(1) placing the volume verification tool on a stable, level surface;

(2) replacing the containment vessels prior to each measurement rather than replacing the vessels after several uses;

(3) keeping the volume verification tool away from any air currents or sources of vibration;

(4) moving the hand-held probe away from the volume verification tool after fluid is introduced into the containment vessels; and (5) using consistent manual fluid transfer techniques with a minimum amount of splashing.

To minimize the down-time of the "ABBOTT PRISM" system and to simplify procedures for using the volume verification tool, it would be desirable to develop an alternative technique for measuring the volume of a liquid dispensed by a liquid-dispensing mechanism.

SUMMARY OF THE INVENTION

In one aspect, this invention provides an apparatus for improving the procedure for quantifying the volume of liquid dispensed by a liquid-dispensing mechanism of an analytical instrument. The apparatus of this invention comprises:

(a) at least one weigh cup;
(b) at least one standard mass;
(c) at least one transducer assembly to convert a value of weight to an electrical response; and
(d) at least one electronic circuit for converting the electrical response to a measurement of volume.

The apparatus requires a source of power to energize the at least one transducer assembly and the at least one electronic circuit. Optionally, the apparatus can have at least one electrical connector to connect the apparatus to an analytical instrument. In addition, the apparatus preferably comprises a housing to protect some or all of the foregoing components of the apparatus. It is preferred that the apparatus have dimensions sufficiently small to fit into a small opening in the analytical instrument that is having its liquid-dispensing mechanisms verified and be sufficiently portable to be capable of being transported to a plurality of locations within the analytical instrument so that a plurality of liquid-dispensing mechanisms within the instrument can be verified. In the case of a large instrument, such as, for example, the "ABBOTT PRISM" system, as many as 41 liquid-dispensing mechanisms must be verified over a distance of as much as seven feet, while the channel opening for receiving the apparatus may have dimensions no greater than 1 inch×4 inches×8 inches.

In another aspect, this invention provides a method for calibrating readings of the volume of liquid dispensed by a liquid-dispensing mechanism of an analytical instrument so that absolute measurements of the volume of liquid dispensed can be obtained. Absolute measurement of the volume of liquid dispensed is needed so that the amount of liquid dispensed is accurate, with the result that subsequent analytical tests can be performed at the appropriate levels of specificity and sensitivity, whereby antigens and antibodies in biological samples can be detected. The method comprises the steps of:

(a) providing an apparatus comprising:
  (1) at least one weigh cup;
  (2) at least one standard mass;
  (3) at least one transducer assembly to convert a value of weight to an electrical response; and
  (4) at least one electronic circuit for converting the electrical response to a measurement of volume;
(b) recording the value of weight of the at least one standard mass;
(c) recording the value of weight of the at least one weigh cup when it is empty; and
(d) computing the gain of the apparatus.

In order to measure the volume of liquid dispensed by means of the thus-calibrated apparatus, the following additional steps can be used:

(e) measuring a plurality of volumes of liquid dispensed in sequence; and (f) calculating the mean value of the volumes of liquid dispensed.

In addition, it is preferred to compensate for the drift of the at least one transducer assembly during the measurements of the volumes of liquid dispensed. It is further preferred to calculate the value of standard deviation from the differences between the individual values of the volumes of liquid dispensed and the mean value of the volumes of liquid dispensed.

The apparatus and method of this invention enable a user to make accurate and precise measurements of the volumes of liquid dispensed in an analytical instrument by means of a portable measuring device, attachable to the analytical instrument. The portable measurement apparatus is effective over a range of operating temperatures and over a range of fluid densities. In addition, the apparatus of this invention makes it possible to verify the volume of liquid dispensed by a dispensing station within about 60 seconds. The apparatus of this invention can itself be calibrated in less than about 30 seconds. Furthermore, the apparatus of this invention allows the verification of a plurality of dispensing stations simultaneously.

BRIEF DESCRIPTION OF THE DRAWINGS

In FIG. 4, the components of the at least one electronic circuit are not shown.

DETAILED DESCRIPTION

Figure 1:
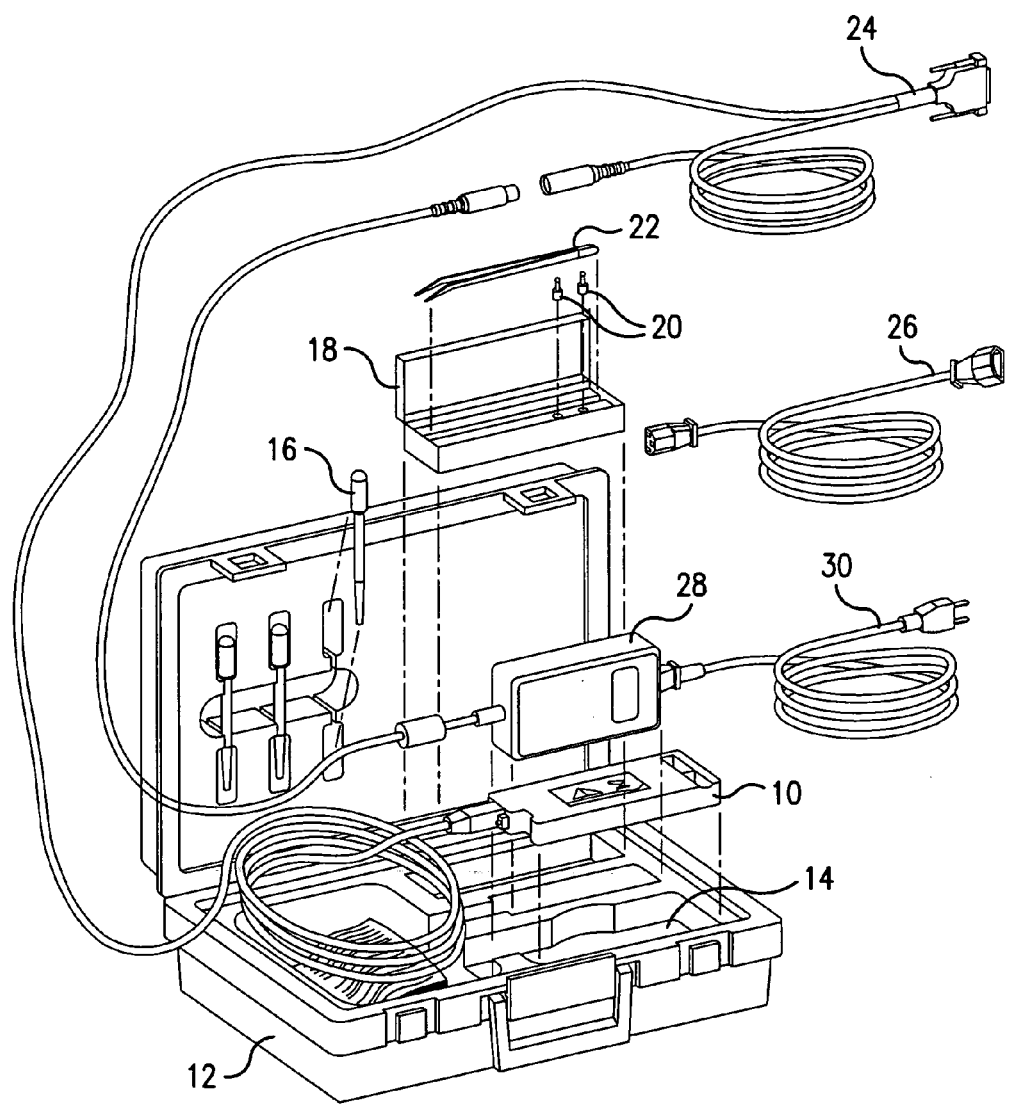
FIG. 1 is an exploded perspective view of the apparatus of this invention in a carrying case.
Figure 2:
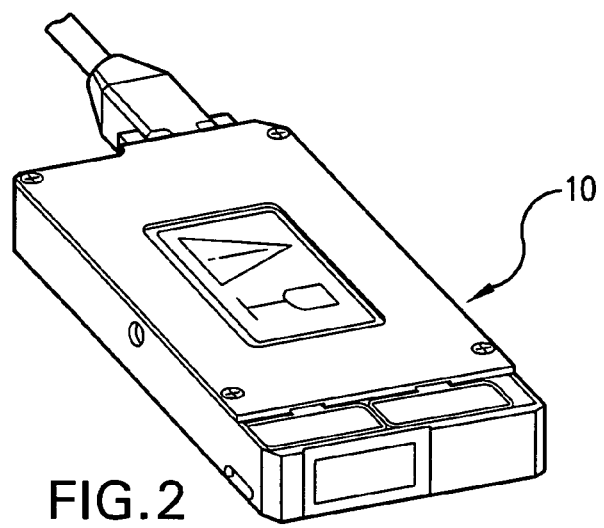
FIG. 2 is a perspective view of the apparatus of this invention.
Figure 3:
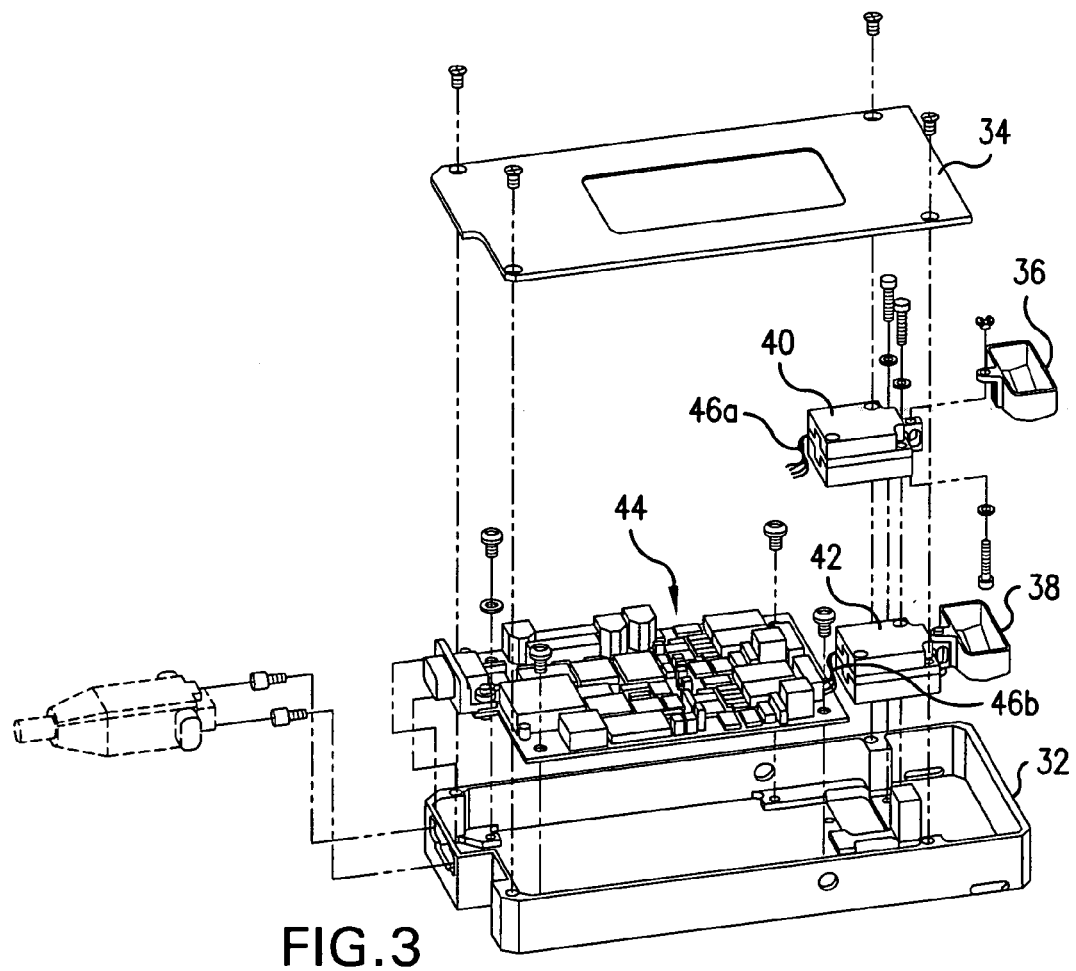
FIG. 3 is an exploded perspective view of the apparatus of this invention.
Figure 4:
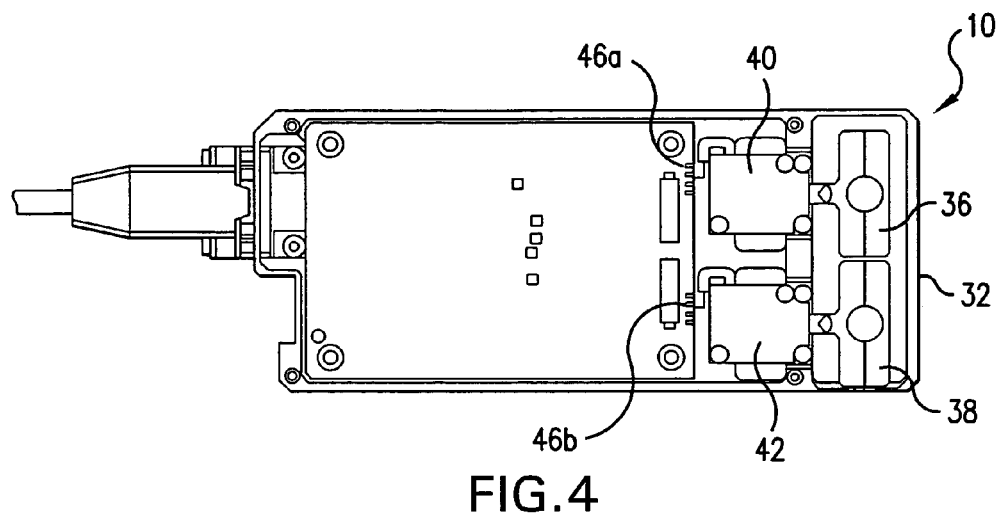
FIG. 4 is a top plan view of the apparatus of this invention, in which the cover is removed.
Figure 5:
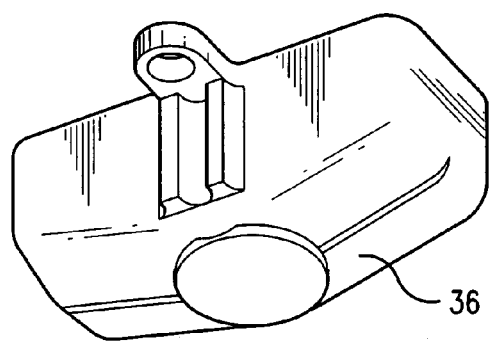
FIG. 5 is a perspective view showing the bottom of the weigh cup of the apparatus of this invention.
Figure 6:
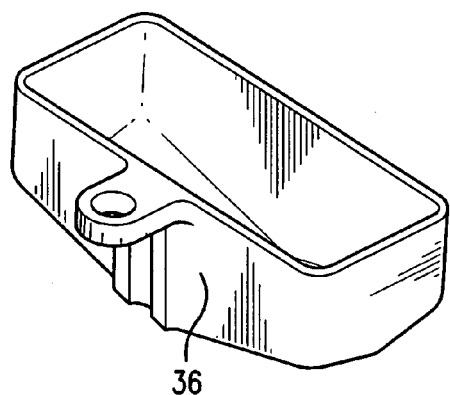
FIG. 6 is a perspective view showing the interior of the weigh cup of the apparatus of this invention.

As used herein, the expression "weigh cup" means a container used to capture liquid from a dispensing location and transfer the weight thereof to a load cell; the expression "standard mass" means a solid, preferably a metallic solid, used as a standard of comparison in weighing. A standard mass having a known weight, such as, for example, three (3) grams, is suitable for use in calibrating the apparatus of this invention prior to performing measurements of the volume of liquid dispensed; the expression "transducer assembly" means a device used to convert a physical response to an electrical response; the expression "load cell" means a specific type of transducer assembly that converts changes in mass (weight) to changes in electrical response. As used herein, the "transducer assembly" is a "load cell".

As used herein, the expression "balancing circuit" means a circuit that provides an adjustable current source to normalize the output offset voltage of a load cell into a range usable by electronic circuits. Normalization allows the use of load cells having wide ranges of offset voltages. The expression "first stage amplifier", and the like, means an instrumentation amplifier that, in conjunction with the balancing circuit, is used to amplify the output of the load cell. The typical gain of the first stage amplification in this invention is 120 Volts/Volt. Any common-mode noise signals from the transducer assembly are minimized by means of an instrumentation amplifier. The expression "second stage amplifier", and the like, means an instrumentation amplifier that is used to subtract the output voltage of the first stage amplifier from the reference voltage to increase the dynamic range of the electronics. The typical gain of the second stage amplification in this invention is 25 Volts/Volt. The expression "gain" means the change in output as a function of the change in input. For example, the change in voltage coming out of an electrical or electronic system can be a function of the change in voltage going into the electrical or electronic system. In this case, the gain is measured in units of Volts/Volt. As another example, the change in voltage coming out of an electrical or electronic system can be a function of the change in mass of a solid being measured by the electrical or electronic system. In the latter case, the gain is measured in units of Volts/gram.

As used herein, the term "filter" means an electric or electronic device that is used to reduce the presence of signals at higher frequencies so that digital sampling may be performed with minimal aliasing and so that unwanted higher frequency components do not interfere with the desired signal. In this invention, a sixth order Butterworth filter designed with a cutoff set near 5 Hz is preferably selected to maximize the filter roll-off characteristics (120 dB/decade) while providing relatively fast response to changes of steady state signals.

As used herein, the expression "A/D converter" means a device used to convert analog signals into corresponding digital codes. In the apparatus of this invention, the A/D converter converts voltages derived from the weigh cup to digital signals. As the number of conversion bits increases, the resolution for the signals being measured also increases.

As used herein, the expression "real time" refers to a manner of processing information wherein the information is processed as the event occurs rather than being stored for processing at a later time.

As used herein, the term "channel", when referring to an analytical instrument that is having its liquid-dispensing mechanisms verified, means a pathway running through the analytical instrument through which the apparatus of this invention can be guided, whereby the apparatus can be positioned under a liquid-dispensing mechanism of the analytical instrument. The term "channel", when referring to the apparatus of this invention, means an electrical pathway for a transducer assembly and the electronics associated with that transducer assembly.

Referring now to FIG. 1, the apparatus of this invention comprises a tray assembly 10, which is shown in a commercial embodiment. The tray assembly 10 can be carried in a case 12 having a foam insert 14, which does not generate static electricity. The case 12 is preferably made from a polymeric material, e.g., polyethylene. The case 12 preferably also contains a transfer pipette 16, a case 18 for containing at least one standard mass 20, a forceps 22 for gripping the at least one standard mass 20, a power cable 24, a first power cord 26, a power pack 28, and a second power cord 30. The values of the standard masses preferably range from about 2 g to about 3.3 g, and are typically 3 g.

Referring now to FIGS. 2, 3, 4, 5, and 6, the tray assembly 10 comprises a tray 32, a cover 34 for the tray 32, a first weigh cup 36, a second weigh cup 38, a first transducer assembly 40, a second transducer assembly 42, and an electronics board 44, preferably an electronics printed circuit board, i.e., electronics PCB. A plurality of transducer assemblies is not required, but a plurality of transducer assemblies is preferred, because measurements of the volumes of liquid dispensed by a plurality of liquid-dispensing mechanisms can be performed simultaneously, thereby resulting in a more rapid verification procedure. When the apparatus is in use, the electronics board 44 is connected to a power supply external to the tray 32, e.g., an external power pack. It is preferred that the tray 32 and the cover 34 be made of an electrically shielding material. The preferred electrically shielding material comprises aluminum, based on cost and ease of machining. The weigh cups 36 and 38 are made of an electrically insulating material, such as, for example, polymeric material. It is preferred that each weigh cup be designed so that the liquid dispensed is centered therein in order to minimize torsional loads and furnish a level platform for the standard masses.

A set of interconnecting cables 46a, 46b is provided to interconnect electrical signals between each transducer assembly (load cell) 40 and 42 and the electronics board 44. The cables 46a, 46b are preferably 4-wire cables. The set of interconnecting cables preferably comprises a total of two cables that can be connected to the connectors on the electronics board. The cable 24 connects a standard communications interface on the electronics board and the analytical instrument, e.g., the "ABBOTT PRISM" system. External power is applied to the electronics board 44 by means of this cable.

Figure 13:
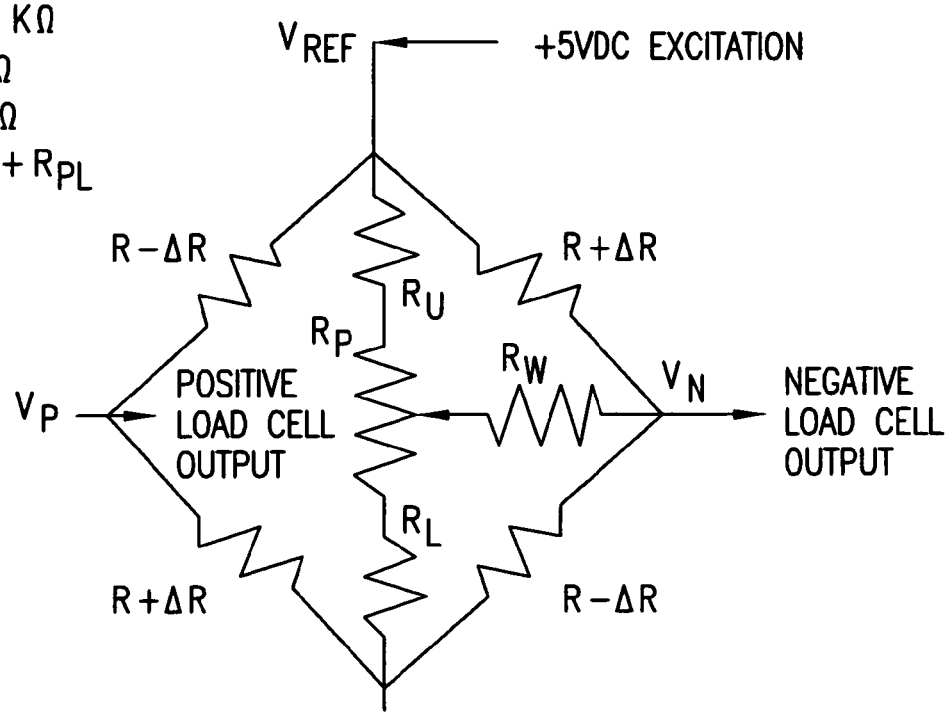
FIG. 13 is a schematic diagram of a Wheatstone bridge and balancing circuit.

Referring now to FIGS. 7, 8, 9, 10, 11, 12, and 13, each transducer assembly 40, 42 comprises a base 50, a beam 52, and a cover 54. The base 50, the beam 52, and the cover 54 are joined together, preferably by means of a plurality of fasteners 56, typically threaded screws. The beam comprises a stationary portion 52a and a movable portion 52b. Strain gauges 60, 62, 64, and 66 are mounted on the movable portion 52b of the beam 52. The use of four strain gauges maximizes sensitivity and provides temperature compensation. Terminals 68, 70, 72, 74, 76, and 78 are mounted on the stationary portion 52a of the beam 52. The four strain gauges 60, 62, 64, and 66 and the terminals 68, 70, 72, 74, 76, and 78 are connected so as to form a Wheatstone bridge. The balancing circuit of the Wheatstone bridge typically comprises a 200-ohm potentiometer and voltage dividing resistors ($R_U$ and $R_L$ in FIG. 13) across the excitation and ground, along with a 5.11 kilo-ohm resistor between the potentiometer arm and the negative output of the load cell. The representation shown in FIG. 13 is well-known to one of ordinary skill in the art.

The strain gauges of the transducer assemblies (load cells) 40, 42 comprise resistive transducers, the resistance of which varies proportionally as a function of strain applied. The resistance R of a strain gauge wire having resistivity $\rho$, cross-sectional area S, and length l is $$R = \rho l/S$$

Straining the wire changes its length to $l+\Delta l$, its cross-sectional area to $S-\Delta S$, and its resistance to $$R+\Delta R = \rho(l+\Delta l)/(S-\Delta S)$$

Because the volume of the strain gauge wire must remain constant, then $$(l+\Delta l)(S-\Delta S) = Sl$$

$$R+\Delta R = \rho(l+\Delta l)^2/Sl$$

$$\Delta R = \rho(l+\Delta l)^2/Sl - \rho l/S$$

$$\Delta R = \rho[(l+\Delta l)^2 - l^2]/Sl$$

$$\Delta R = \rho(2l\Delta l + \Delta l^2)/Sl$$

$$\Delta R = \rho(2\Delta l + \Delta l^2/l)/S$$

$$\Delta R = \rho\Delta l(2+\Delta l/l)/S$$

Fractional elongation per weight applied for the load cell used herein is about 400 microstrains per 10 g, or about 2 microstrains per 50 mg change in weight. Thus, the error in dropping the term $\Delta l/l$ is 0.1 ppm per 50 mg change in weight (which is negligible), that is, $\Delta l/l \ll 2$. Therefore, $$\Delta R = \rho(2\Delta l)/S$$

$$\Delta R = SR(2\Delta l)/Sl, \text{ and}$$

$$\Delta R = 2R\Delta l/l$$

where R represents the unstrained resistance and $\Delta l/l$ represents the fractional elongation, which is dimensionless, but is typically in the range of parts per million change or "microstrains."

Strain gauges are explained in detail in *The Way Things Work*, Vol. 2, Simon and Schuster (New York: 1971), pp. 480–483, incorporated herein by reference.

Figure 7:
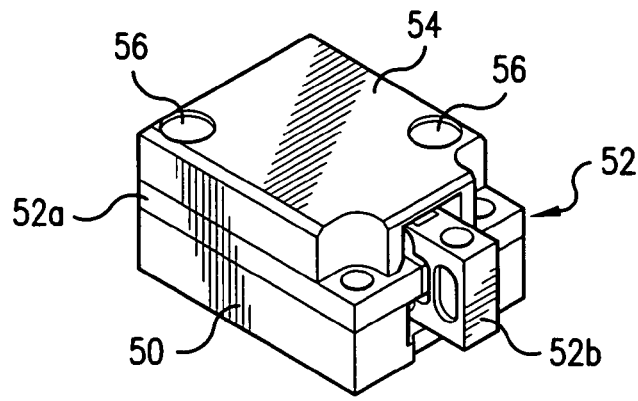
FIG. 7 is a perspective view of the strain gauge assembly of the apparatus of this invention, shown completely assembled.
Figure 8:
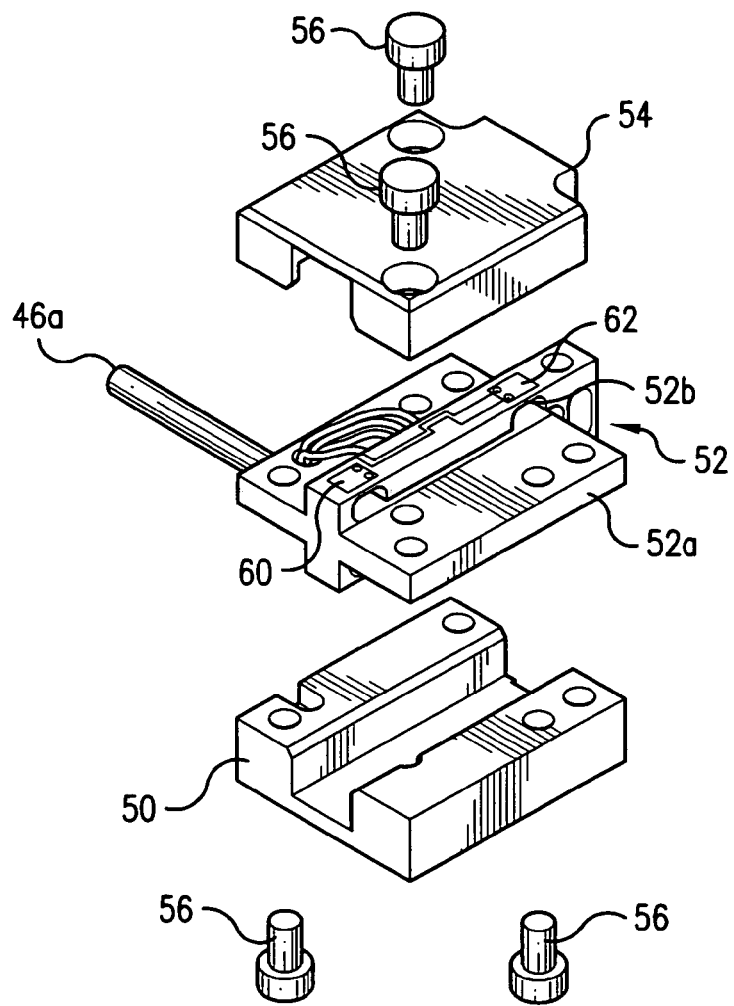
FIG. 8 is an exploded perspective view of the strain gauge assembly of FIG. 7.
Figure 9:
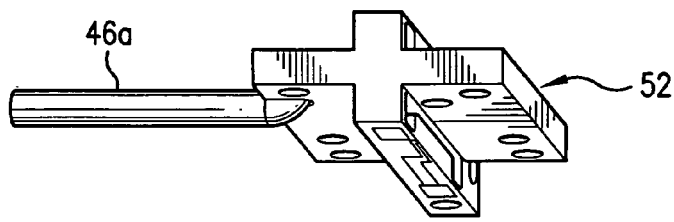
FIG. 9 is a perspective view of the underside of the beam of the strain gauge assembly of FIG. 7.
Figure 10:
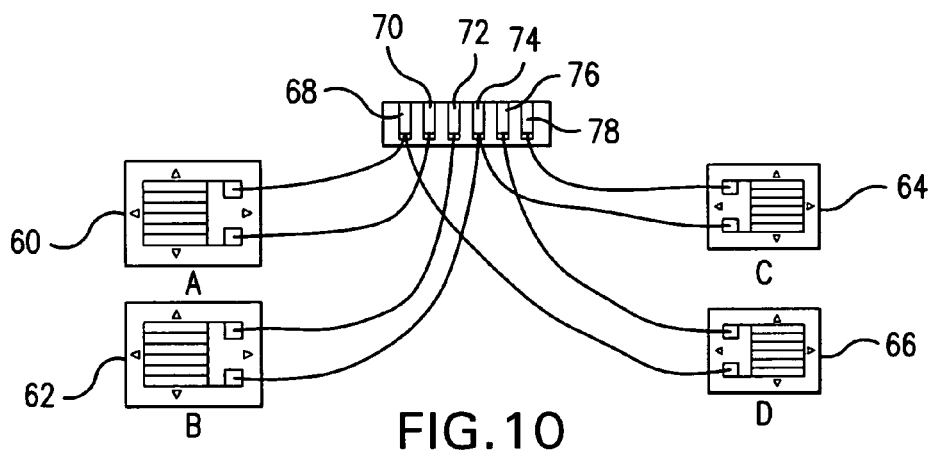
FIG. 10 is a schematic view of the strain gauge assembly of the apparatus of this invention.
Figure 11:
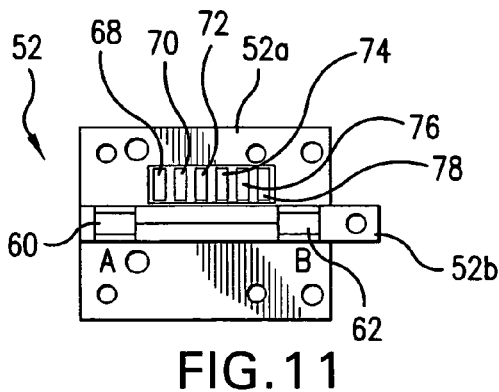
FIG. 11 is a top plan view of the beam of the strain gauge assembly of FIG. 7.
Figure 12:
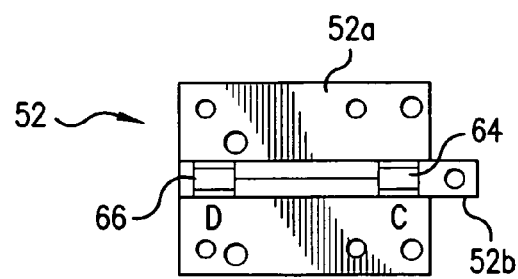
FIG. 12 is a bottom plan view of the beam of the strain gauge assembly of FIG. 7.

A strain gauge can be fabricated by depositing resistive material on a flexible backing according to a pattern that maximizes fractional elongation for a given strain. Strain gauges are sensitive to temperature. If the strain gauges are arranged in pairs, they can compensate for each other's temperature variations (provided that both strain gauges are at the same temperature, i.e., there is no temperature gradient across the pair). Additional temperature compensation for the drift of the output voltage of the load cell resulting from shifts in temperature can be provided by an algorithm programmed into the software of the apparatus. Thermal barriers can partially compensate for heat generated by the load cell itself and changes in ambient temperature, such as, for example, those changes experienced when the tray assembly is inserted into a channel of the analytical instrument. Such thermal barriers are shown in FIGS. 7 and 8 as reference numerals 50 and 54. Additional thermal barriers can be used as desired.

Referring to the schematic diagram of the load cell (FIG. 13), the bridge excitation voltage is denoted as $V_B$. By voltage division, the positive ($V_P$) and negative ($V_N$) bridge outputs of the bridge are:

$$V_P + V_B(R+\Delta R)/(R+\Delta R+R-\Delta R) = V_B(R+\Delta R)/2R$$

$$V_N = V_B(R-\Delta R)/2R$$

so that $$V_P - V_N = V_B \Delta R/R$$

Therefore, the use of four strain gauges applied to the arms of the bridge maximizes the gain of the transducer assembly (load cell) and provides compensation for changes in temperature. The use of four strain gauges produces four times the cell sensitivity as compared to use of a single strain gauge. The electronics board 44 provides an additional gain "A" so that the output of the weigh cup is:

$$V_{CUP} = A V_B \Delta R/R$$

The sensitivity of the apparatus of this invention is given by the ratio of the change in $V_{CUP}$ to the change in applied weight, and is preferably at least 1.2 volts per gram, more preferably 1.35 volts per gram.

Although the strain gauges 60, 62, 64, and 66 occupying the four arms of the bridge have nominally equal resistances at no mechanical load, these values of resistance will not be exactly equal, due mainly to the weight of the empty weigh cup, and there will be an offset voltage at the output of the load cell. On account of this phenomenon, balancing circuits are used on the electronics board so that offset voltages of the load cells are adjusted to a desired value before amplification is performed. Adjusting the offset voltages before amplification (using potentiometers in the balancing circuits) allows the use of a fixed gain to each instrumentation amplifier on the electronics board 44.

The electronics board 44 supplies the bridge excitation to the load cells in the form of a precision 5 VDC power source. An individual bridge excitation signal is provided for each of the two load cells 40, 42 to minimize any cross talk between channels, i.e., the electrical pathways for a transducer assembly and the electronics associated with that transducer assembly. As used herein, "cross talk" means that the electronic response from one weigh cup inadvertently affects the electronic response from the other weigh cup.

Detailed design specifications for the transducer assemblies (load cells) are derived from the functional requirement for an accuracy of ±1.5% and a coefficient of variation (CV) of less than or equal to 1.5% over increments of applied weight of 50 mg from 0 to 0.5 g or over increments of applied weight of 300 mg from 0 to 3 g, in order to allow for measurements for ten dispensations of liquid and known densities of solutions used for measurements of volume of liquid dispensed.

Typical standards for the strain gauges of the apparatus of this invention are set forth in Table I.

TABLE I

| | |
|---|---|
| Weight capacity | 10 g (without cup and associated hardware) |
| Natural frequency with 2.6 g weigh cup | 60 to 120 Hz |
| Sensitivity | 140 to 165 microstrains per gram |
| Rated output | 0.8 to 1.0 mV/V |
| Nonlinearity | 0.05% of rated output |
| Hysteresis | 0.05% of rated output |
| Nonrepeatability | 0.05% of rated output |
| Zero balance | 1.0% of rated output |
| Settling time for 99% rise | 1.0 sec |
| Temperature effect on zero | 0.03% of rated output per ° C. |
| Terminal effect on output | 0.02% of rated output per ° C. |
| Terminal resistance | 350 ohms |
| Maximum excitation voltage | 10 VDC |
| Safe overload | 150% of rated output |
| Deflection inches | 0.004 of rated output |

Figure 14:
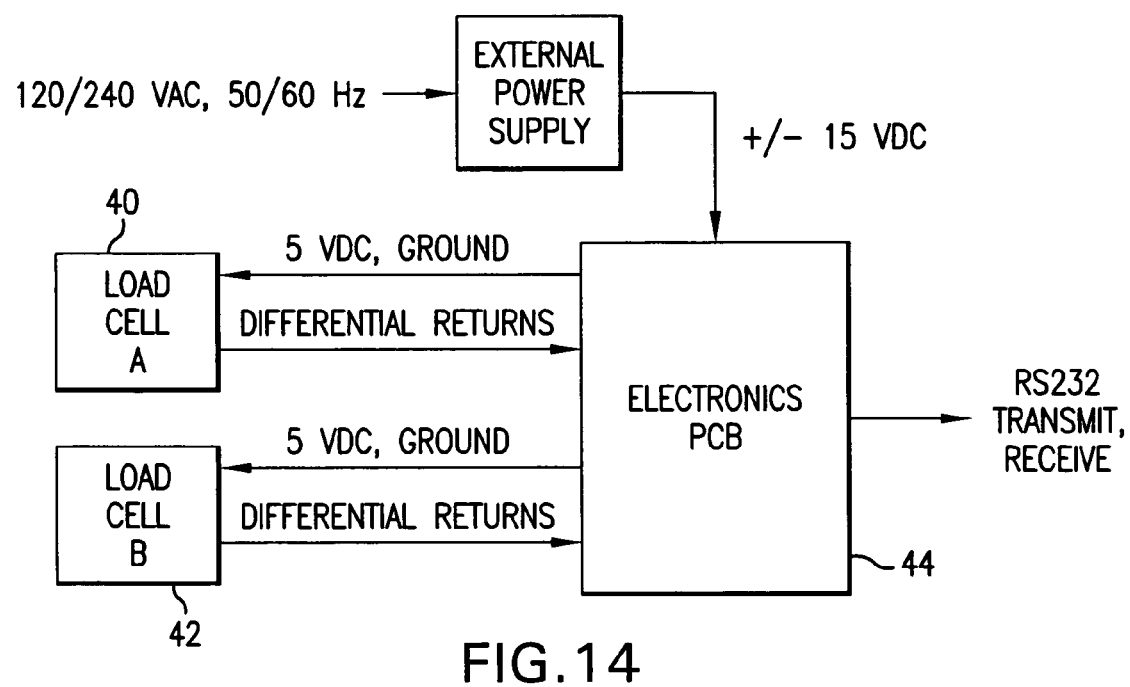
FIG. 14 is a block diagram showing the arrangement of the load cells of the apparatus of this invention. In this invention, each transducer assembly is a load cell.
Figure 15:
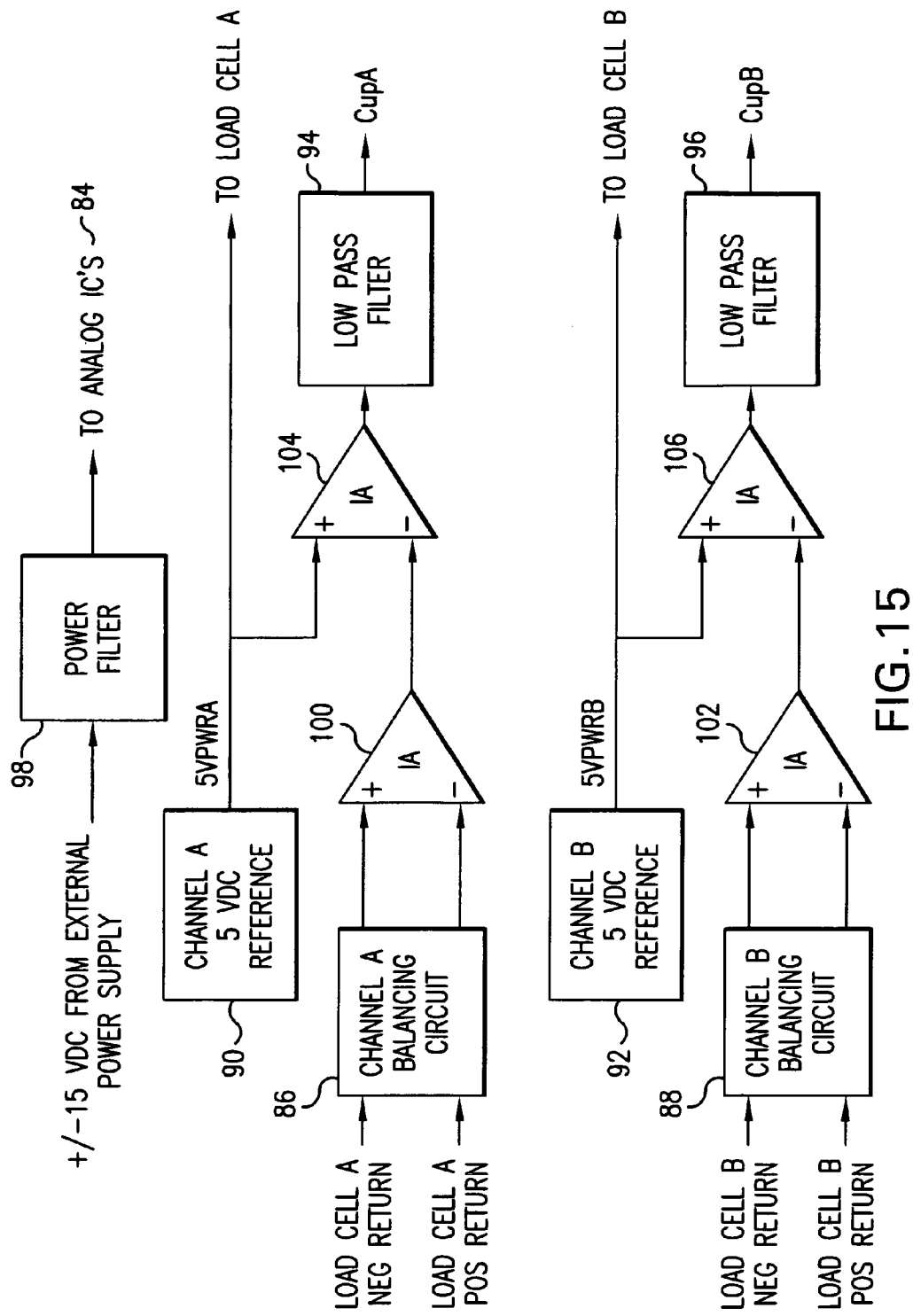
FIG. 15 is a block diagram showing the analog electronics section of the electronic board of the arrangement of FIG. 14.

Referring now to FIG. 14, the tray assembly 10 comprises a first transducer assembly (load cell) 40 and a second transducer assembly (load cell) 42. The load cells 40 and 42 are connected to an electronics board 44 located with the tray assembly 10. The electronics board 44 includes an analog electronics section (not shown) and a digital electronics section (not shown). Referring now to FIG. 15, the analog electronics section 84 of the electronics board 44 includes a balancing circuit 86 for channel A and a balancing circuit 88 for channel B, a 5 VDC reference 90 for channel A and a 5 VDC reference 92 for channel B, a low pass filter 94 for channel A and a low pass filter 96 for channel B, a power filter 98, a first instrumentation amplifier 100 for channel A and a first instrumentation amplifier 102 for channel B, and a second instrumentation amplifier 104 for channel A and a second instrumentation amplifier 106 for channel B. High accuracy instrumentation amplifiers provide required gain with negligible nonlinearity, while low pass filters provide noise rejection with steep rolloff above the cutoff frequency.

A 5 VDC internal power for the analog electronics can be created by regulating and filtering the 15 VDC internal power. Preferably, separate 5 VDC power sources 90, 92 are maintained for the transducer assemblies (load cells) 40, 42 and analog electronics to minimize cross talk between channels. Preferably, a 5 VDC power source (not shown) is maintained for the digital electronics separate from the analog electronics to minimize noise coupling between analog and digital electronics. The 15 VDC internal power can be created by filtering 15 VDC external power. The 15 VDC internal power lines are used only by analog electronics.

In the analog electronics section 84, two 5 VDC power sources 90, 92 can be used, one for each channel. The total current draw from each precision 5 VDC reference is preferably less than 20 mA. The output of each load cell is directed into the first stage of amplification. Each output of the first stage of amplification is adjusted to a nominal value of approximately 4.9 VDC by use of the potentiometer of the balancing circuit. Each output of the second stage of amplification is created from the amplified difference between the precision 5 VDC reference and output of the first stage of amplification. These voltages, one output for each channel, will be in the range 0 to 10 VDC for the standard masses applied to the weigh cups, the standard masses preferably being in the range 0 to 3.3 g. Voltages of the weigh cups are those voltages that are the output of the second stages of amplification and that have been filtered by the low pass filter.

The analog electronics section 84 of the electronics board provides each of the following components or functions:
 (1) power filtering to reduce or remove noise from the 15 VDC supply voltages before use by the amplifiers in the analog electronics section;
 (2) precision 5 VDC references for exciting the Wheatstone bridges of the load cells, as a source of energy for the balancing circuits, and providing the voltage references for the second stages of amplification;
 (3) balancing circuits to adjust the offsets of the Wheatstone bridges of the load cells before amplification;
 (4) two-stage amplification to provide precision amplification of the outputs of the load cells;
 (5) low pass filters to eliminate higher frequency noise.

Figure 17:
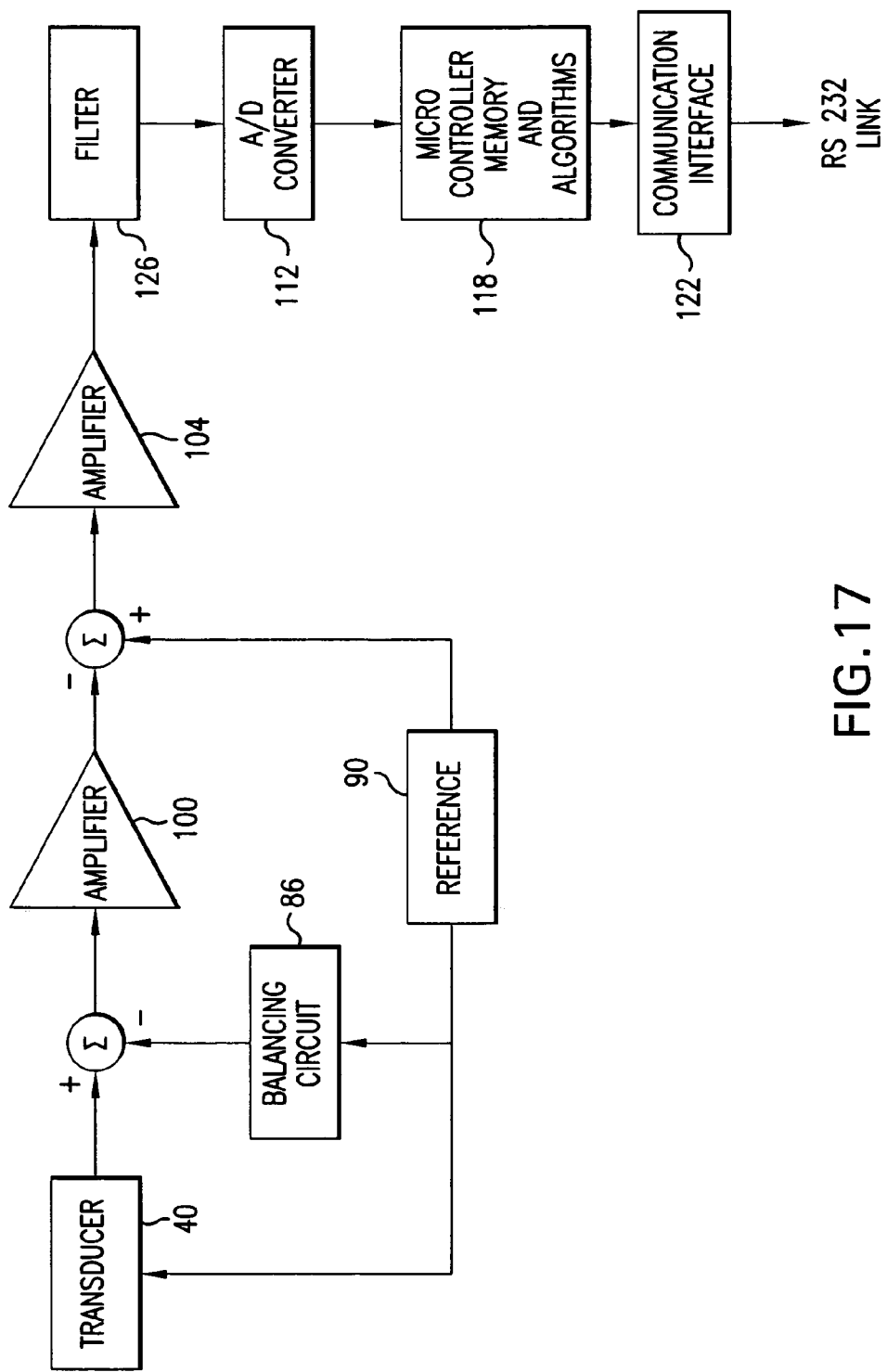
FIG. 17 is a block diagram showing the flow of electrical signals during use of the apparatus of this invention.

Preferably, the balancing circuits 86 and 88 can adjust the offset voltage of the bridge (i.e., noncompliance between strain gauge resistances with the empty weigh cup) to within 1 mV of the desired value, given a 5 VDC bridge excitation. The desired value is obtained by setting the offset voltage of the bridge so that an empty weigh cup results in an approximately 4.9 VDC output from the first stage of amplification (approximately 0.1 volt less than the 5 VDC reference to the first stage). Once adjusted, the balancing circuit maintains the desired value of offset voltage to within 0.43 µV (which equates to approximately 1 mg) over a ten second period. Preferably, the balancing circuit, balancing circuit 86 or balancing circuit 88, does not by itself draw more than 2.5 mA from the 5 VDC excitation source. The preferred requirements can be achieved by using a balancing circuit consisting of a 200-ohm multi-turn potentiometer with voltage dividing resistors across the excitation and ground, along with a 5.11 kilo-ohm resistor between the potentiometer arm and the negative bridge output. FIG. 17 illustrates how the balancing circuit interacts with the 5 VDC references and the instrumentation amplifiers for one transducer assembly. The following table describes the two stages of amplification for a preferred embodiment.

TABLE II

| | |
|---|---|
| Gain of first stage | 120 Volts/Volt ±1% |
| Gain of second stage | 25 Volts/Volt ±1% |
| Gain temperature coefficient | 110 ppm/° C. |
| Nonlinearity of first stage | 78 ppm |
| Nonlinearity of second stage | 55 ppm |
| Drift | ±2.5 µV/° C. |
| Input offset voltage | ±60 µV |

TABLE II-continued

| | |
|---|---|
| Input bias current | ±30 nA |
| Input noise | 0.8 µV peak to peak, 0.01 to 10 Hz |
| Minimum CMR | 106 dB from DC to 60 Hz |
| Minimum slew rate | 1.0 V/µs |
| Settling time (0.01%) | 500 µs |

The total gain, i.e., the transfer function of the electronics only, is preferably 3000 Volts/Volt±2%. The total gain plus the transfer function of the transducer assembly supports a nominal sensitivity of 1.35 Volts/gram. Because total nonlinearity is within 133 ppm, the variation in accuracy due to amplification nonlinearity over a 50 mg weight increment is less than 0.01 mg and over a 300 mg weight increment is less than 0.05 mg. The low pass filter is preferably a 6th Order Butterworth Filter having a cutoff frequency near 5 Hz.

Figure 16:
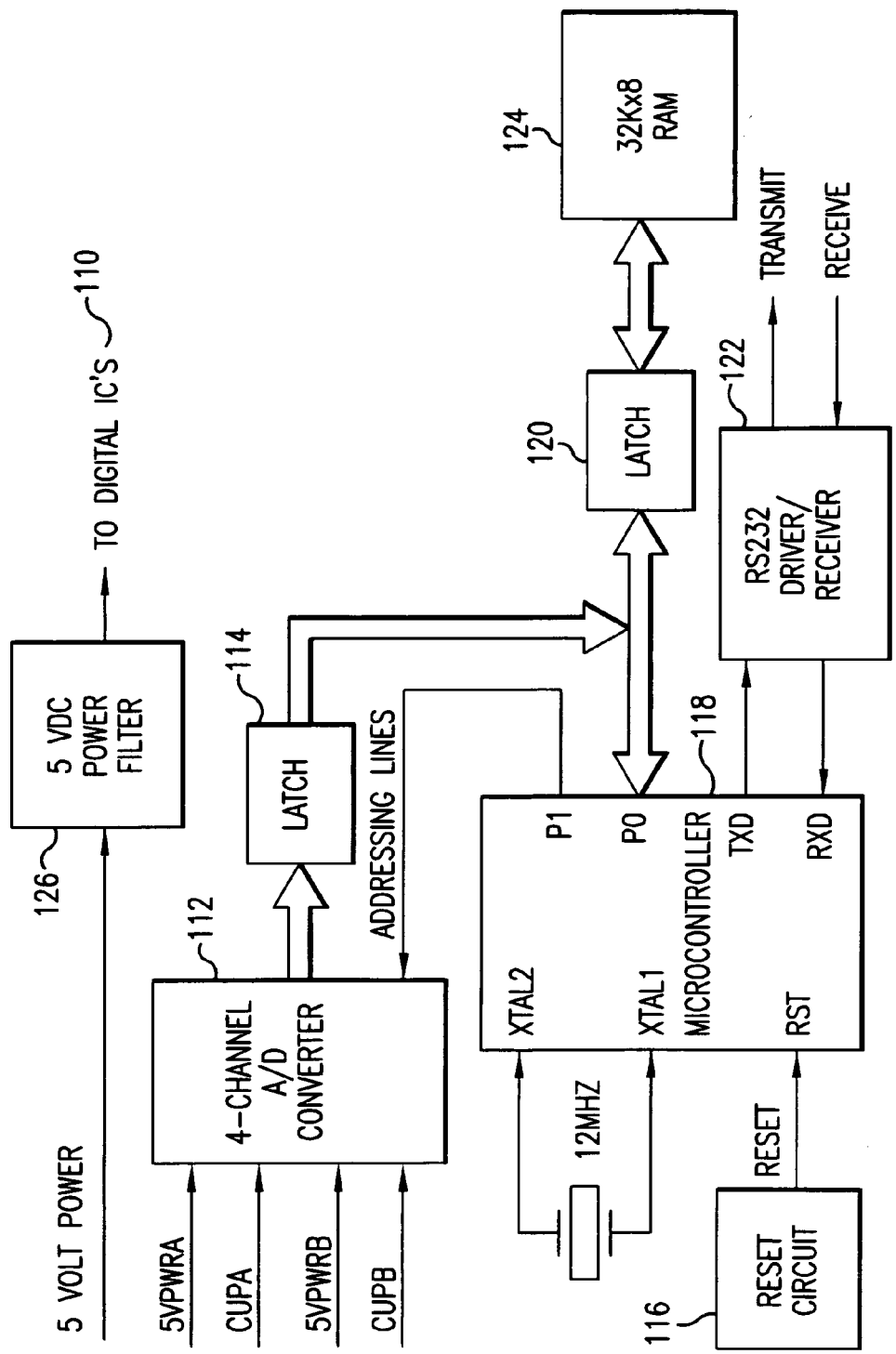
FIG. 16 is a block diagram showing the digital electronics section of the electronic board of the arrangement of FIG. 14.

Referring now to FIG. 16, the digital electronics section 110 of the electronics board 44 includes an A/D converter 112, a latch 114, a reset circuit 116, a microcontroller 118, a latch 120, a driver/receiver 122, and Random Access Memory (RAM) 124. The circuit also includes a 5 VDC power filter 126 to minimize the disturbances that are generated by the digital circuits from interfering with the incoming power. These circuit components are described in more detail in Horowitz and Hill, *The Art of Electronics*, Second Edition, Cambridge University Press (Cambridge, UK: 1989), incorporated herein by reference. The microcontroller 118, preferably a 89C51 microcontroller, processes signals from the A/D converter 112, preferably a 4-channel 16-bit A/D converter, and communicates with the analytical instrument, such as, for example, the "ABBOTT PRISM" system, via a communications interface, preferably a driver/receiver 122, such as, for example, a RS232 driver/receiver.

In a preferred embodiment, a 4-channel A/D converter is used. Two channels are used to measure the two weigh cup voltages, and two channels are used to monitor the two 5 VDC analog reference voltages. The input range is preferably −10 to +10 volts. The A/D converter 112 preferably has 16-bit conversion. Although the tri-state outputs are present on the parallel port, an intermediate latch is preferably used between the parallel output and the microcontroller because the bus may be active during conversion. In this invention, conversion speed is preferably in the range of 25 µs, which allows data conversion rates sufficient for sampling each load cell 200 times per second. In this invention, it is preferred that accuracy be within the range ±2.0 LSB (0.012% of unipolar full scale).

The microcontroller 118 is preferably an 8-bit microcontroller containing a minimum of 64K bytes of on-chip program memory that can be programmed electrically and can be reprogrammed electrically. The microcontroller 118 is preferably capable of simultaneously obtaining voltages of two weigh cups sampled at a minimum rate of 200 Hz in real time while also supporting bi-directional communication with the computer of the analytical instrument.

The reset circuit 116 contains a low voltage monitor circuit to detect when the digital power supply voltage falls below 4.6 VDC nominal and sends a reset signal to the microcontroller 118. The reset circuit can employ an RC On-Time delay circuit using a resistor and a capacitor to form a slowly exponentially rising voltage, which is used to hold the microcontroller reset for a sufficient period of time to allow for a supply that has a fast turn-on time. If desired, a manual reset button can be used to manually reset the microcontroller 118. The reset circuit 116 allows the microcontroller 118 to operate under known and controlled power conditions and provides a controlled sequence to power up the apparatus of this invention. It is preferred that an LED be provided to indicate the status of the microcontroller 118.

The driver/receiver 122, preferably RS-232 driver/receiver, provides the means for the apparatus of this invention to communicate with the computer of the analytical instrument to provide the information relating to the volume of liquid dispensed. The driver/receiver 122 provides a mechanism to receive commands from the analytical instrument and return processed data. The driver/receiver 122 preferably employs the RS232 communications standard. The driver/receiver 122 and the microcontroller 118 allows communication messages to be stored until the microcontroller 118 becomes available after having performing other functions for which the timing is critical.

Figure 18:
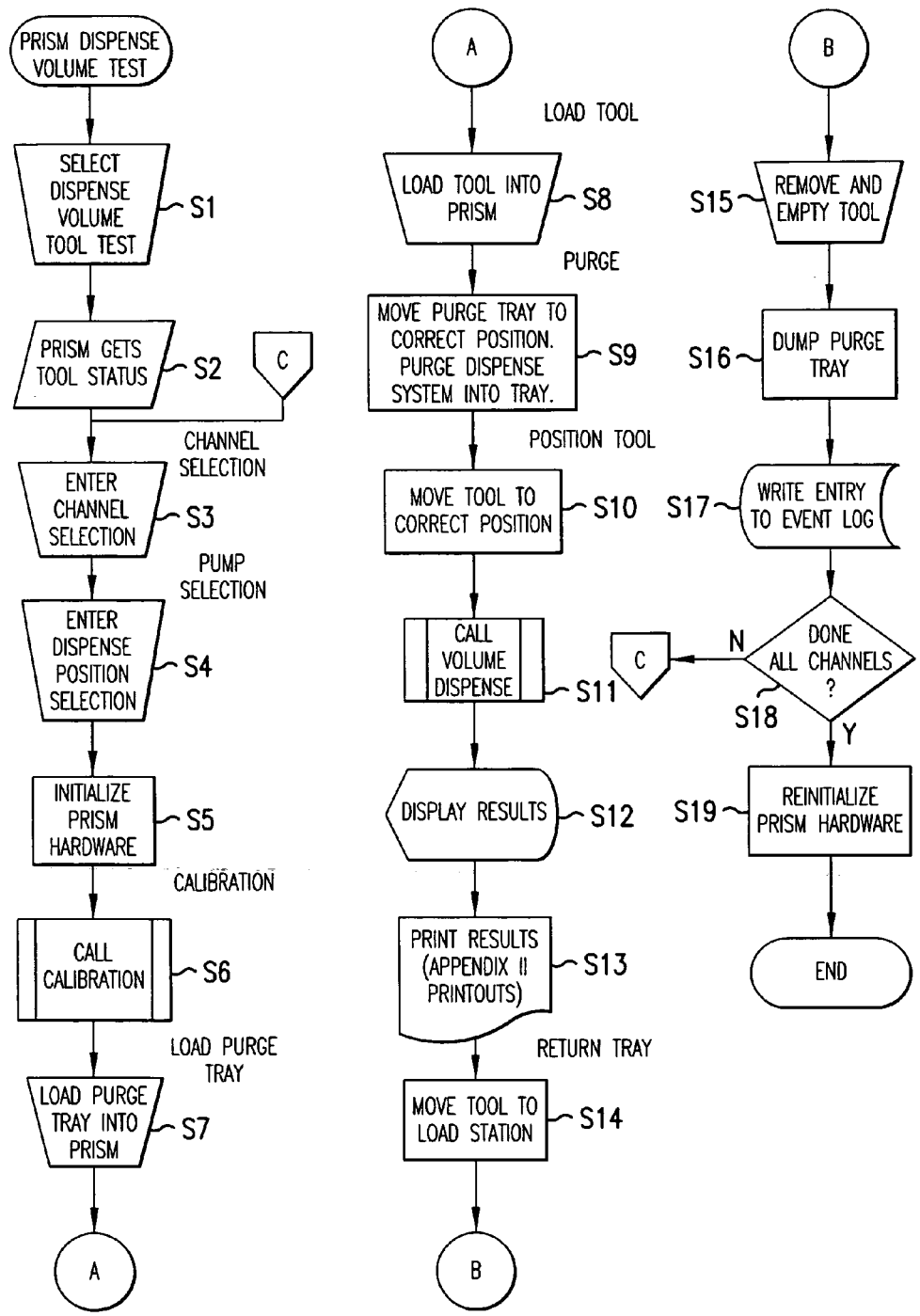
FIG. 18 is a flow chart showing the steps involved in measuring the volume of liquid dispensed by a liquid-dispensing mechanism of an analytical instrument by means of the calibrated apparatus of this invention.

It is preferred that certain algorithms be executed by means of software programmed into the microcontroller 118. It is also preferred that additional memory in the form of random access memory (i.e., external random access memory) be employed for performing computations while the main program is operating. External random access memory allows computer programs to be executed at higher speeds. In particular, it is preferred that the microcontroller 118 be capable of executing an algorithm for determining the volume of liquid dispensed from a liquid-dispensing mechanism. One such algorithm, the steps of which are illustrated in FIG. 18, preferably includes the following steps:

(a) recording the reading of the voltage after a standard mass of known value has been inserted into a weigh cup;
(b) recording the reading of the voltage of the empty weigh cup after the standard mass is removed from the weigh cup;
(c) computing the gain of the apparatus;
(d) dispensing a sequence of volumes of liquid into the weigh cup and reading the voltage of the weigh cup, while compensating for drift of the voltage readings;
(e) converting the voltage readings to values of the volume of liquid dispensed by taking into account the density of the liquid dispensed;
(f) calculating the absolute volume for each volume of liquid dispensed by means of the gain of the apparatus and the measurement in step (d);
(g) repeating steps (d), (e), and (f) for a plurality of dispensations (preferably ten) of the liquid;
(h) calculating the mean value of volume for a plurality of dispensations of the liquid;
(i) calculating the standard deviation for the plurality of dispensations of the liquid, preferably by means of the following formula:

$$\sqrt{\sum_{j=1}^{n} (\text{Dispense Volume}(j) - \text{Mean Dispense Volume})^2/(n-1)}$$

Figure 21:
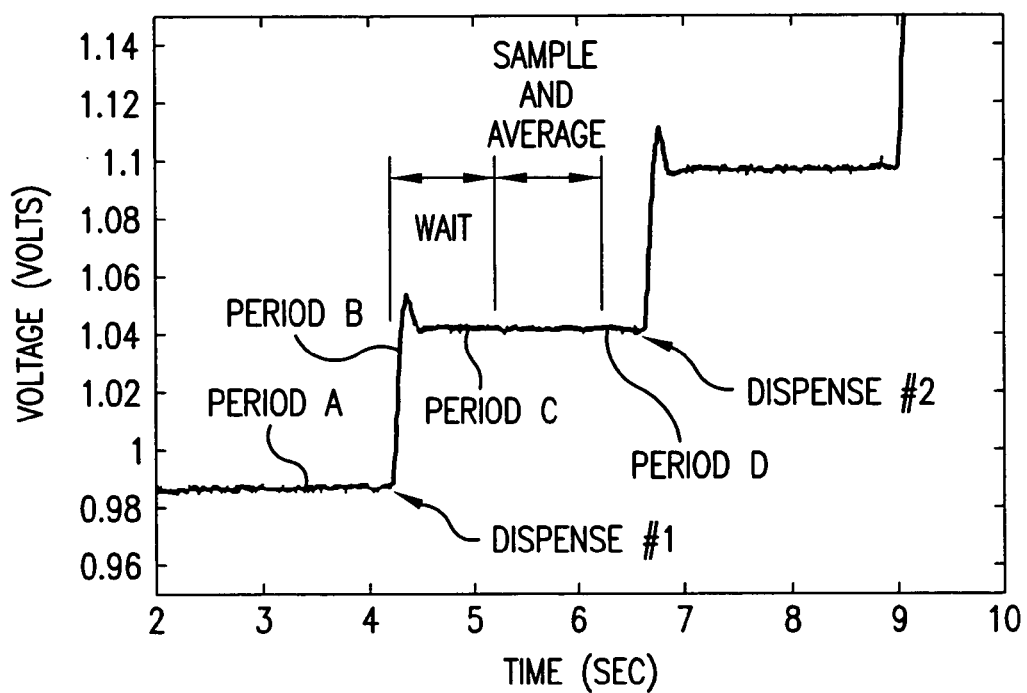
FIG. 21 is a graph showing a typical profile of voltage as a function of time for the operation of dispensing an actual volume of liquid into a weigh cup.

Step (d) of the foregoing procedure, which is illustrated in FIG. 21, preferably involves the following steps:
(a) continuously measuring the voltage of the weigh cup for a period of time prior to the dispensing of the liquid (Period A);
(b) dispensing a volume of liquid into the weigh cup;
(c) detecting a monotonic increase (i.e., an increase that never decreases in value) in the value of the voltage of the weigh cup above a threshold voltage over a period of time (Period B);
(d) measuring a period of delay from the moment that the threshold voltage is detected to allow time for the liquid to settle after the liquid is dispensed into the weigh cup (Period C);
(e) repeatedly measuring the voltage of the weigh cup for a period of time subsequent to the period of delay (Period D);
(f) computing the mean value of the voltage of the weigh cup for the period of time prior to dispensing the liquid;
(g) re-computing the mean value of the voltage of the weigh cup for the period of time prior to dispensing the liquid upon discarding a certain number of individual readings deemed to constitute noise;
(h) computing the mean value of the voltage of the weigh cup for the period of time subsequent to dispensing the liquid;
(i) re-computing the mean value of the voltage of the weigh cup for the period of time subsequent to dispensing the liquid upon discarding a certain number of individual readings deemed to constitute noise; and
(j) computing the difference between the mean value of the voltage of the weigh cup prior to dispensing the liquid (step g) and the mean value of the voltage of the weigh cup subsequent to dispensing the liquid (step i).

A 5 VDC power source is maintained for the digital electronics, separate from the analog electronics. The total current draw from the digital 5 VDC power source is preferably less than 100 mA.

While not required to meet the preferred specifications, it is preferred that the apparatus of this invention be capable of being run within thirty minutes, preferably within ten minutes, of being powered up. The apparatus can measure weights of up to 3.3 g. If desired, the apparatus can measure weights in excess of 3.3 g. The weight of the empty weigh cup in combination with attachment hardware is typically 2.6 g. The coefficient of variance, CV, which is a measure of the precision of the apparatus, preferably does not exceed 1.5%, based upon an average (arithmetic mean) of a plurality of individual readings, preferably ten in number.

The coefficient of variance is given as $$CV = \left(\frac{\sigma}{\bar{x}}\right)(100)$$

where $\bar{x}$ is the mean of the plurality of readings and $\sigma$ is the standard deviation of the plurality of readings. Accuracy of the apparatus is preferably within ±1.5% over its range of measurement, based upon an average of ten individual readings. The circuits of the apparatus preferably employ regulated 15 Volt DC power supplies and several 5 Volt DC power supplies. The apparatus generates the 5 Volt DC power by means of on-board regulator devices. The regulated 15 Volt DC power supplies are contained in an external universal power pack that can be powered from worldwide voltages ranging from 90 to 264 VAC, 47 to 63 Hz, 0.2 A maximum.

It is preferred that the apparatus have dimensions sufficiently small to fit into a small opening, i.e., a channel, in the analytical instrument that is having its liquid-dispensing mechanisms verified and be sufficiently portable to be capable of being transported to a plurality of locations within the analytical instrument so that a plurality of liquid-dispensing mechanisms within the instrument can be verified. In the case of a large instrument, such as, for example, the "ABBOTT PRISM" system, as many as 41 liquid-dispensing mechanisms must be verified over a distance of as much as seven feet, while the channel opening for receiving the apparatus may have dimensions no greater than 1 inch×4 inches×8 inches. Load cells having the required linearity and load range plus the housing of the apparatus can preferably fit into this space requirement. In fact, the channel opening for receiving the apparatus in the "ABBOTT PRISM" system has a height of about 0.8 inch.

The weigh cups and housing are preferably able to withstand exposure to corrosive fluids such as, for example, the following solutions (which are used with the "ABBOTT PRISM" system): sample diluent buffers, Cysteine solution, transfer wash solutions, probe solutions, probe wash solutions, conjugate solutions, conjugate wash solutions, activator solutions, i.e., (hydrogen peroxide, sodium hydroxide), activator line treatment solution, purge solutions (Proclin), TEAH, and isopropyl alcohol.

OPERATION

Figure 19A:
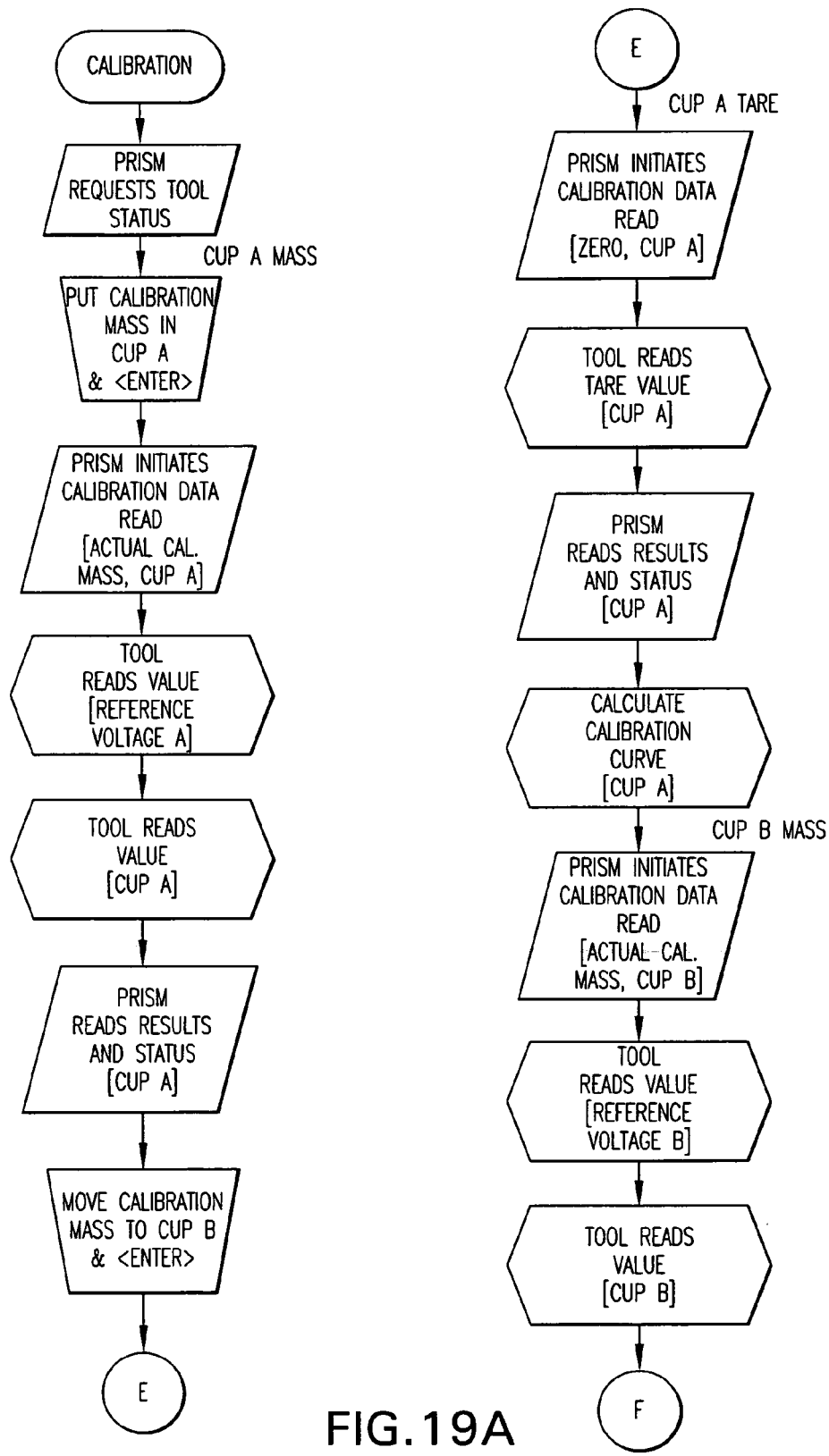
FIG. 19 is a flow chart showing a set of steps involved in calibrating the apparatus of this invention.
Figure 19B:
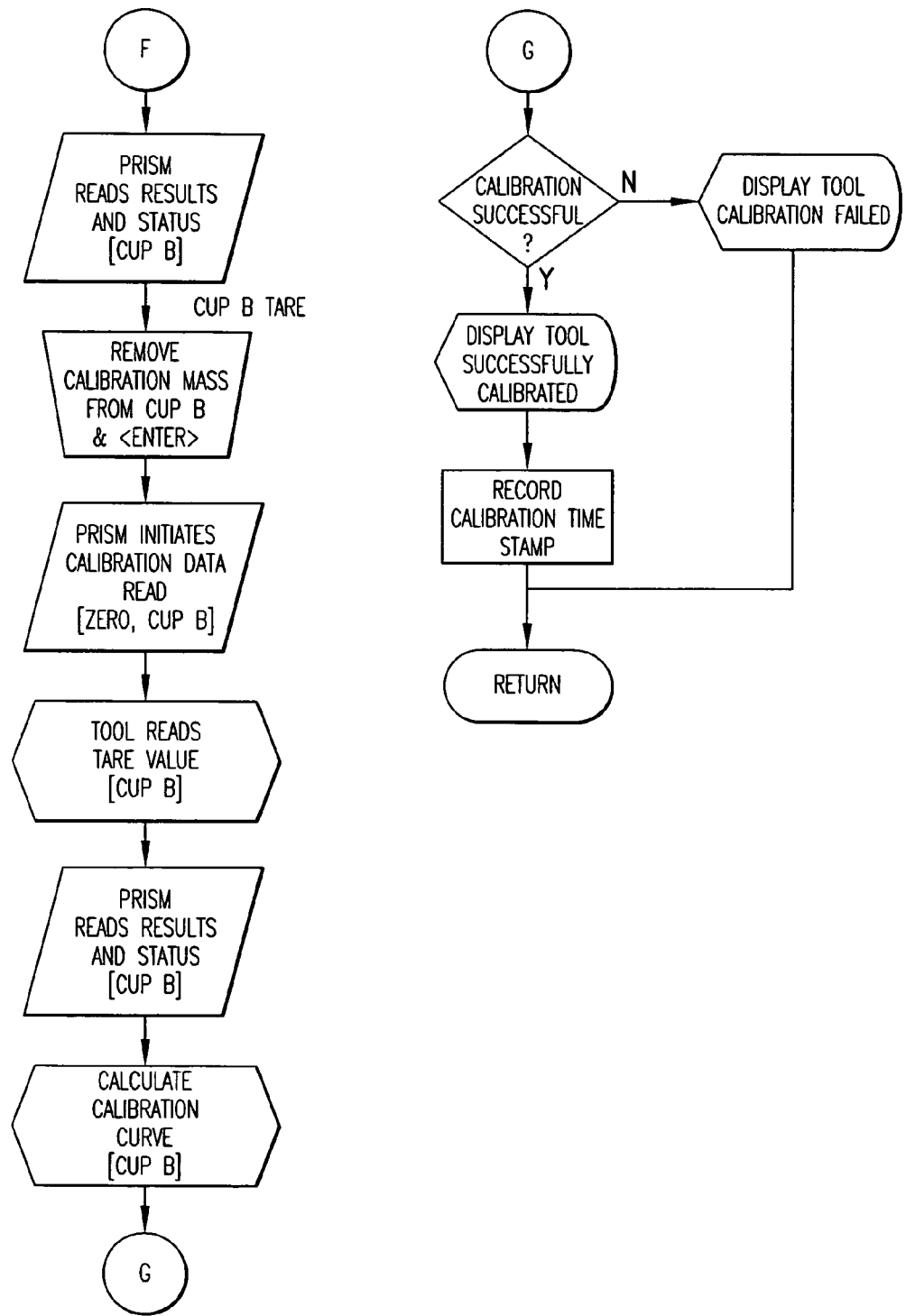
Figure 20:
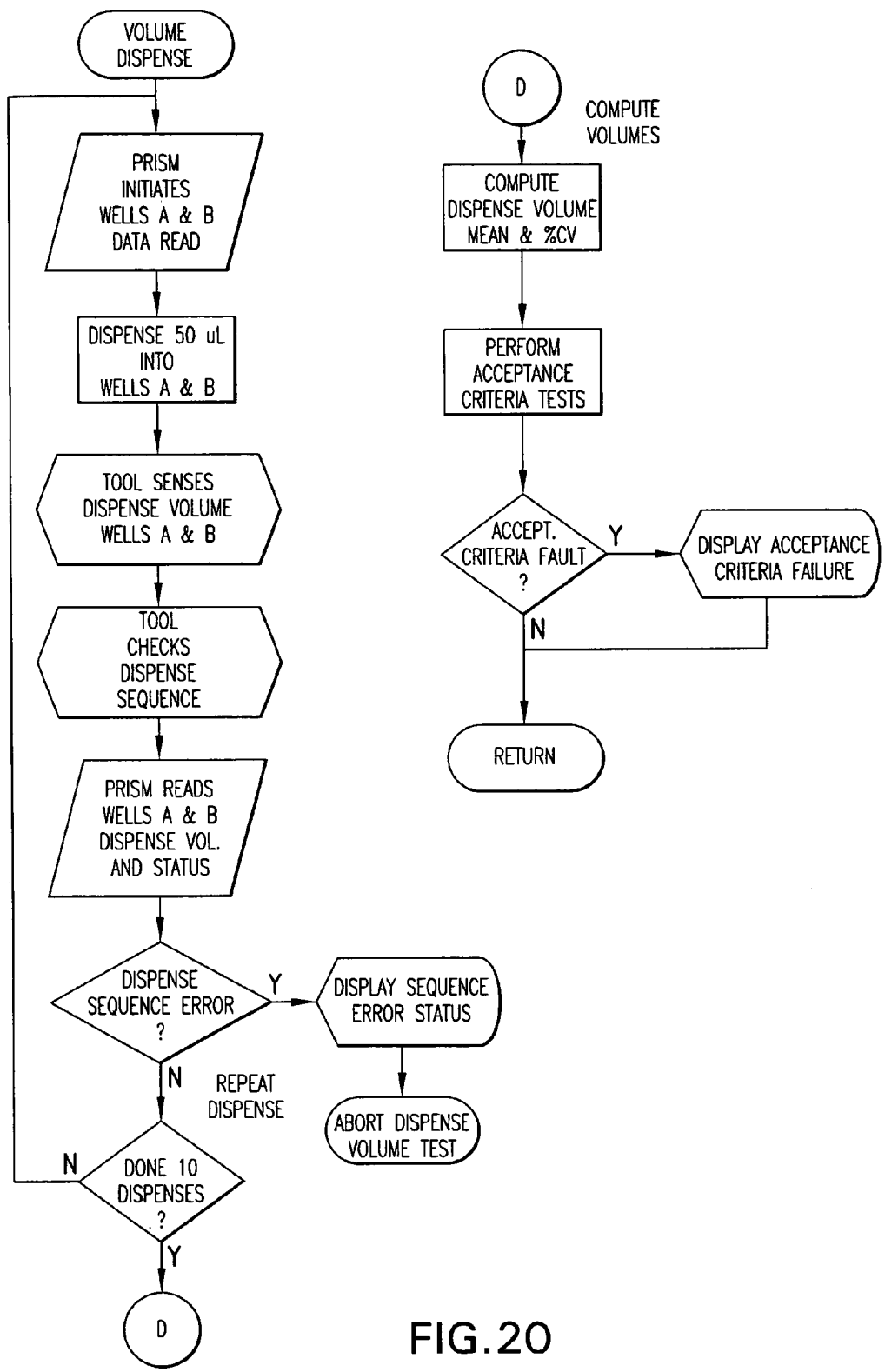
FIG. 20 is a flow chart showing a set of steps involved in converting a measurement of the weight of a liquid to the volume of a liquid by means of a calibration curve and the value of density of the liquid by using the apparatus of this invention.

FIGS. 18, 19, and 20 are flow charts showing steps for verifying the volume(s) of liquid dispensed by liquid-dispensing mechanism(s), e.g., sample probes, metering pumps, of an analytical instrument. In FIGS. 18, 19, and 20, the term "tool" means the apparatus of this invention; the term "PRISM" means the analytical instrument; the term "call" means gaining access to a certain area or module of software; the term "purge" means an aqueous solution used to measure the volume of a liquid and a method for using the aqueous solution; the expression "load station" means the region of an analytical instrument where the apparatus of this invention can be placed temporarily until the apparatus of this invention is moved through a channel of the analytical instrument to a position under a liquid-dispensing mechanism of the analytical instrument; the term "cup" means the weigh cup; the expression "tare value" means the weight of the weigh cup after the standard mass is removed therefrom; the expression "reference voltage" means the voltage derived from the precision 5 VDC reference 90, 92; and the term "well" means the weigh cup.

FIG. 18 shows a preferred procedure for measuring the volume of liquid dispensed by means of calibration data obtained from the procedures illustrated in FIGS. 19 and 20. According to FIG. 18, the volume dispensing features of an analytical instrument, i.e., "ABBOTT PRISM" system, are verified in the following manner:
 (a) the channel of the instrument to be tested is selected (see step S3);
 (b) the liquid-dispensing mechanism to be tested is selected (see step S4);
 (c) the apparatus of this invention is calibrated, typically by the method illustrated in FIG. 19 (see steps S5 and S6);
 (d) after a purge tray is properly positioned, the liquid-dispensing mechanism being tested is requested to dispense liquids, typically by the method illustrated in FIG. 20 (see steps S7 through S11);
 (e) preferably, the results of the verification run is displayed and printed (see steps S12 and S13);
 (f) in the same manner, additional liquid-dispensing mechanisms can be verified for other channels of the analytical instrument (see steps S15 through S19).

FIG. 19 shows a preferred procedure for using standard masses to calibrate the apparatus of this invention. According to FIG. 19, a calibration curve for each weigh cup of the apparatus is prepared by determining the gain of each channel of the apparatus. The gain for a given channel of the apparatus is determined over the range from the point in which the given weigh cup of the apparatus contains a standard mass to the point in which the given weigh cup of the apparatus contains no standard mass, i.e., when the weigh cup is empty. A calibration curve is prepared for each weigh cup of the apparatus.

FIG. 20 shows a preferred procedure for measuring the volume of liquid dispensed by a liquid-dispensing mechanism of an analytical instrument by means of the apparatus of this invention. According to FIG. 20, a calibration curve for a given channel of the apparatus is prepared by dispensing a plurality of volumes of liquids into a given weigh cup of the apparatus and then computing the mean and coefficient of variation (CV) for the volumes of liquid thus dispensed. The procedure shown in FIG. 20 can be used to convert the weight of liquid dispensed to volume of liquid dispensed by means of the calibration curve calculated by the method shown in FIG. 19 and knowledge of the density of the liquid dispensed.

When a dual port pump is subjected to the verification procedure of this invention, it is preferred that the apparatus of this invention be capable of indicating whether a given dispensation occurred on a given channel (e.g., weigh cup 34, channel A) before that dispensation occurred on the other channel (e.g., weigh cup 36, channel B).

The microcontroller 118 estimates the weight of each volume of liquid dispensed based upon the average of voltage readings taken over a period of time prior to the dispensing of liquid (preferably one second) and over a period of time after the dispensing of liquid (preferably one second), as shown in FIG. 21. This procedure allows for transient settling of the dynamics associated with the dispensing of the liquid and the motion of the liquid. After noise is removed from the data, the mean value of the data obtained during the period of time prior to the dispensing of liquid and the mean value of the data obtained during the period of time subsequent to the dispensing of liquid are used as the input to the linear fit relating voltage and weight, as established from the voltage reading of the empty weigh cup and the voltage reading obtained when the weigh cup contains the standard mass. The details of this procedure were described previously in the description of the function of the microcontroller 118. After the analytical instrument is prepared, a plurality of dispensations is performed (preferably ten), and a computer, preferably included with the analytical instrument, computes the average of the readings taken and the CV of the readings taken. Accuracy and precision of the results are as set forth previously. After the analytical instrument is prepared, it is preferred that less than five minutes be required to verify the volume of liquid dispensed at each liquid-dispensing station.

The portable measurement apparatus of this invention is effective over a range of operating temperatures, e.g., 15° C. to 45° C., and over a range of fluid densities. The two densities used for the "ABBOTT PRISM" system are 0.9976 g/ml and 0.9980 g/ml. The apparatus of this invention will allow the use of densities that are of any value, i.e., densities significantly different from 1.000 g/ml are allowed. In addition, the apparatus of this invention makes it possible to verify the volume of liquid dispensed by a dispensing station within about 60 seconds. The apparatus of this invention can itself be calibrated in less than about 30 seconds. Furthermore, the apparatus of this invention allows the verification of a plurality of dispensing stations simultaneously.

The following procedure can be used to test the apparatus, without the need to dispense liquids. The voltage of the weigh cup when empty and the voltage of the weigh cup when containing a standard mass is determined to establish a linear fit relationship between voltage and mass. A set of standard masses of known value (preferably 50 mg per standard mass), preferably consisting of ten standard masses in number, is added, one standard mass at a time, to the weigh cup. The sequence of voltages from the weigh cup reported by the apparatus can be averaged to determine if the average value is within the preferred range of 1.5% of 50 mg for the set of standard masses added to the weigh cup. The CV is computed from the plurality of standard masses added and is preferably less than or equal to 1.5%.

The following non-limiting examples illustrate circuits that can be used to carry out this invention.

EXAMPLES

Figures 1, 22:
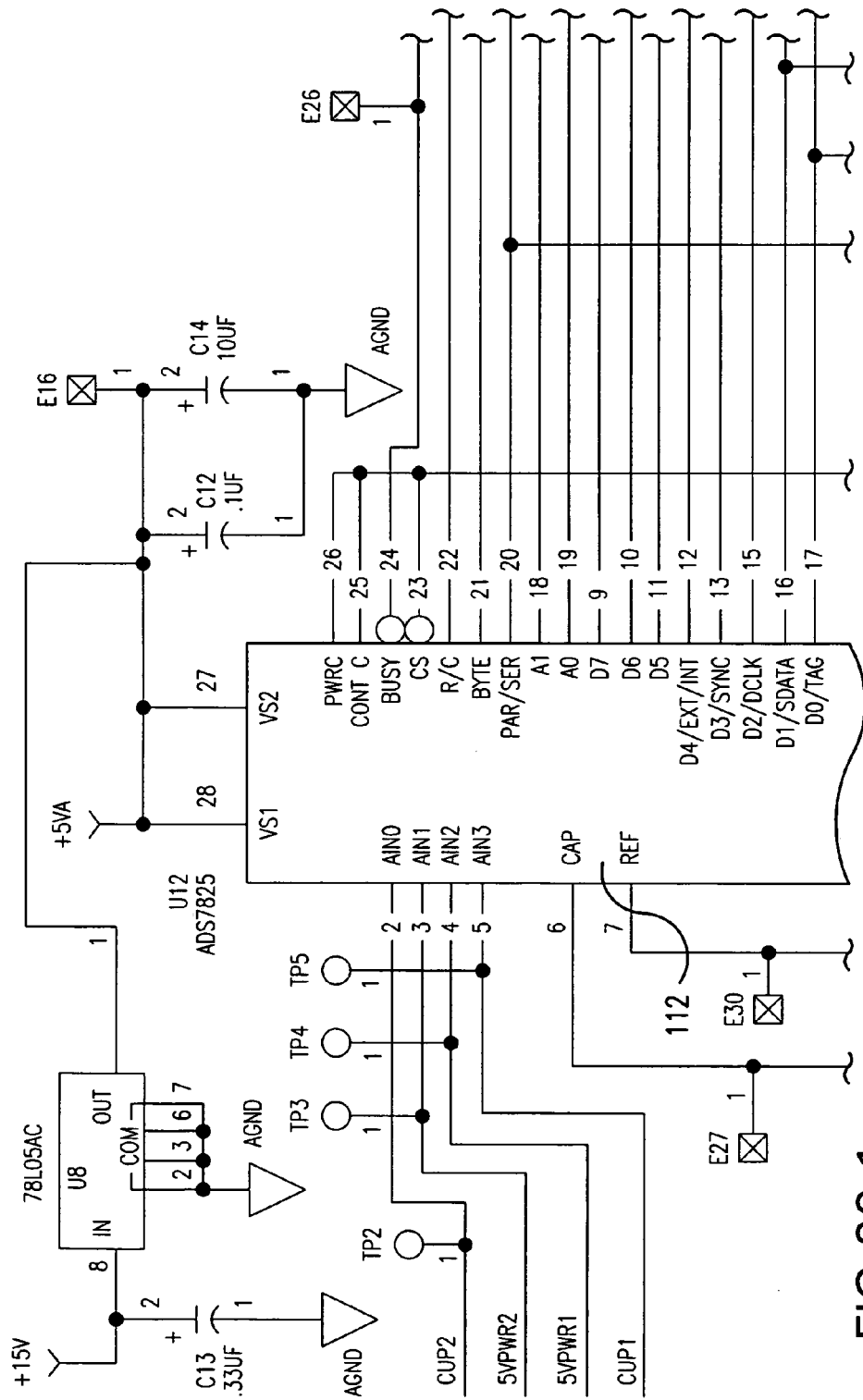
FIGS. 22, 23, 24, and 25 are schematic diagrams of circuits that can actually be used to perform the functions of this invention.
Figures 2, 22:
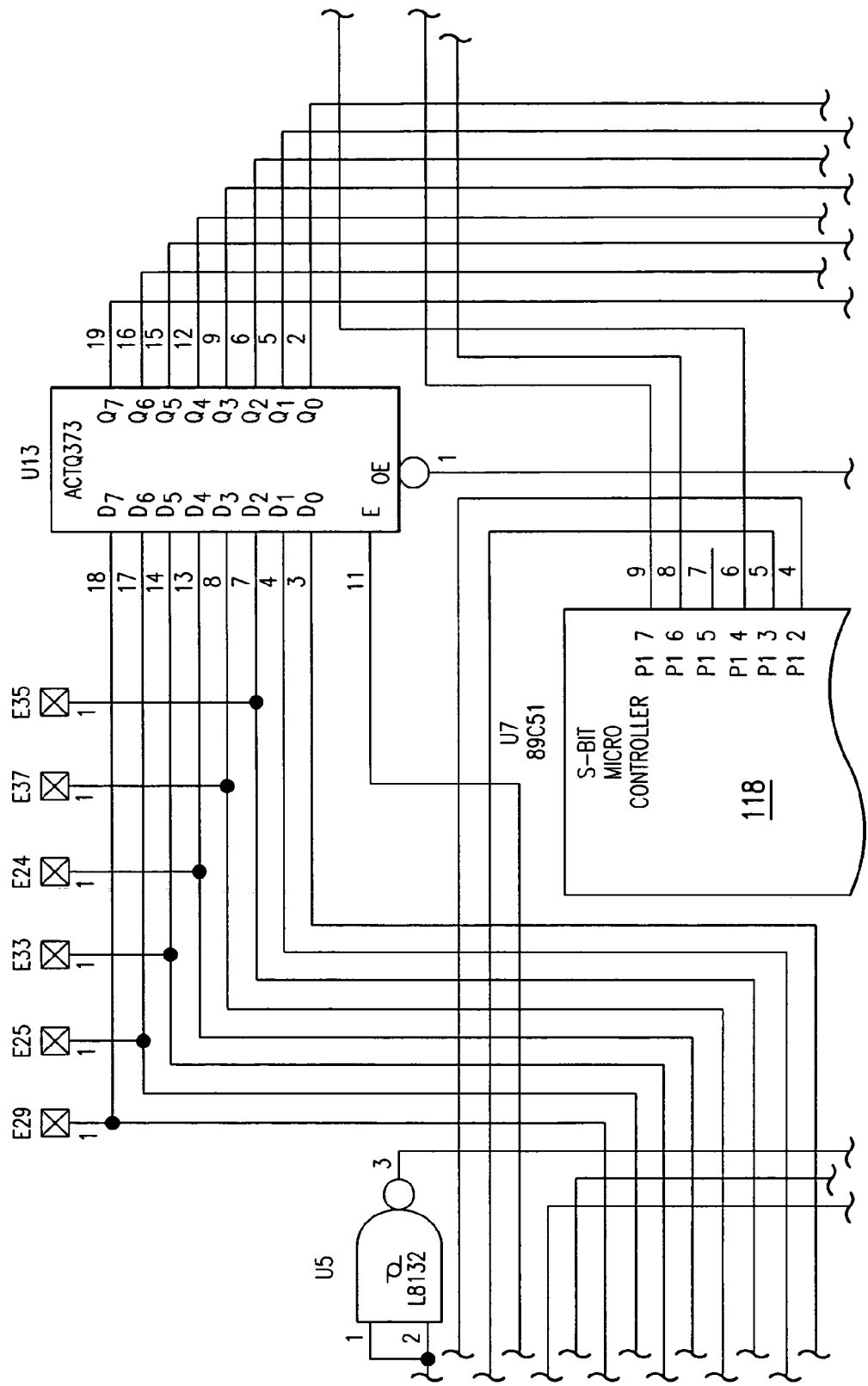
Figures 4, 22:
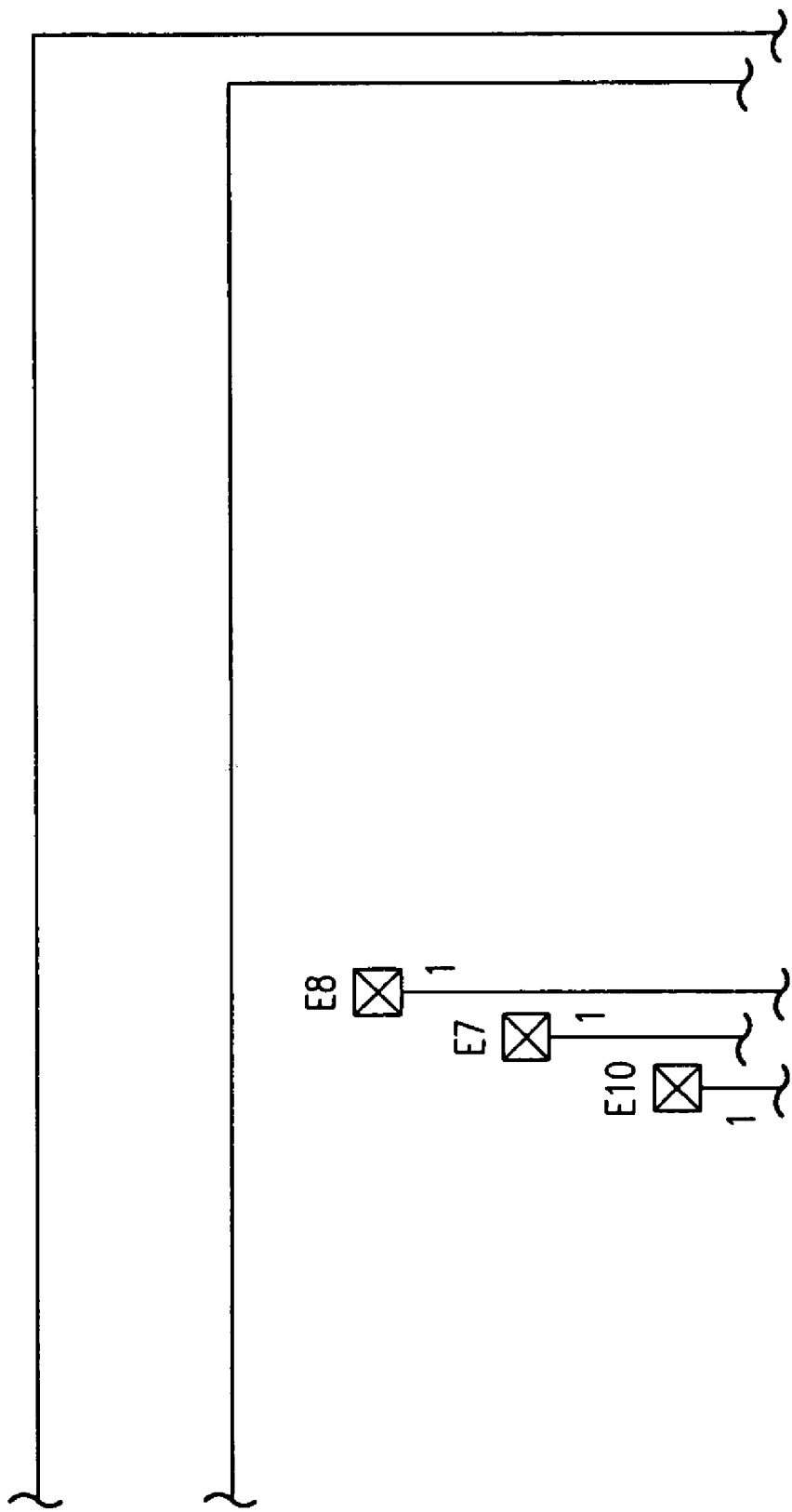
Figures 5, 22:
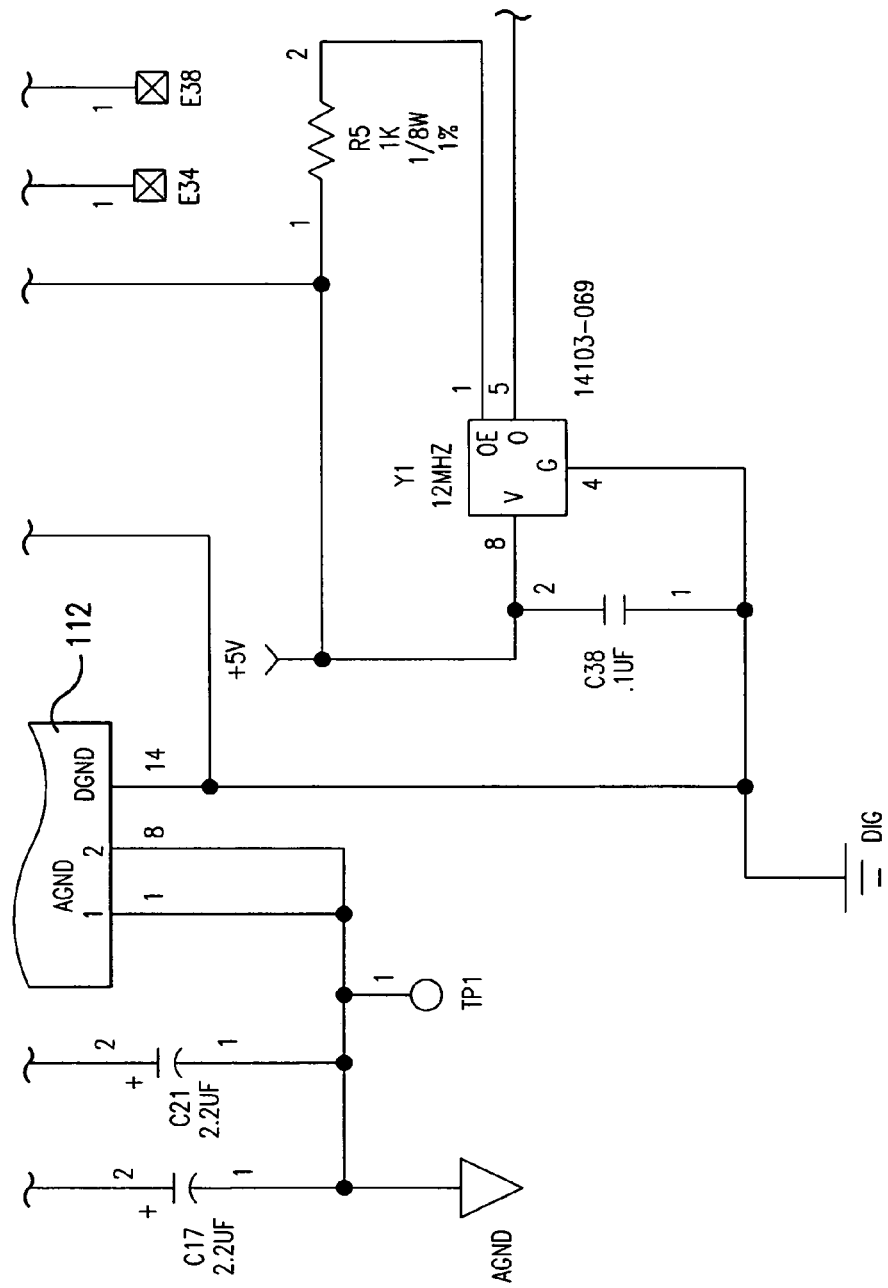
Figures 6, 22:
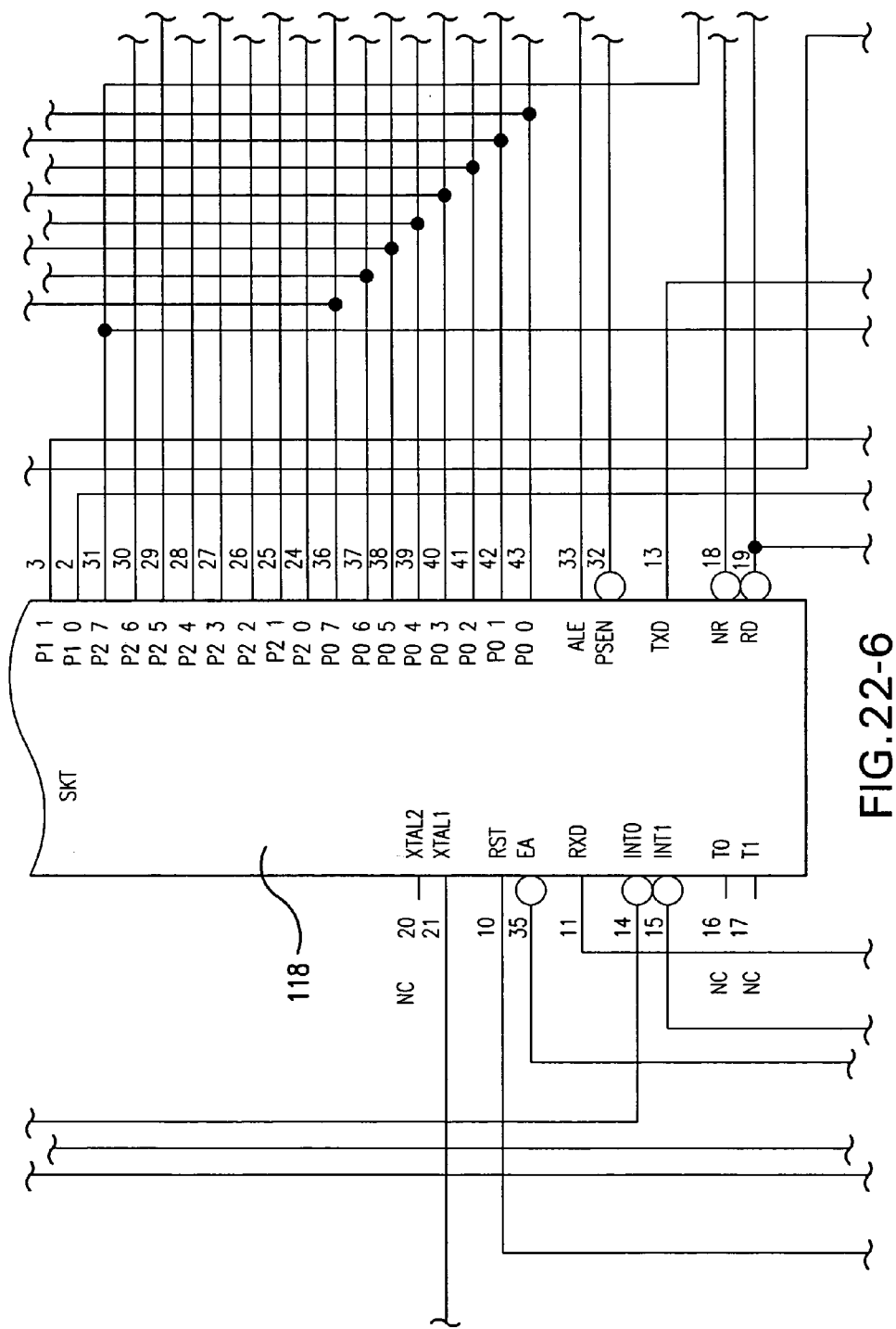
Figures 7, 22:
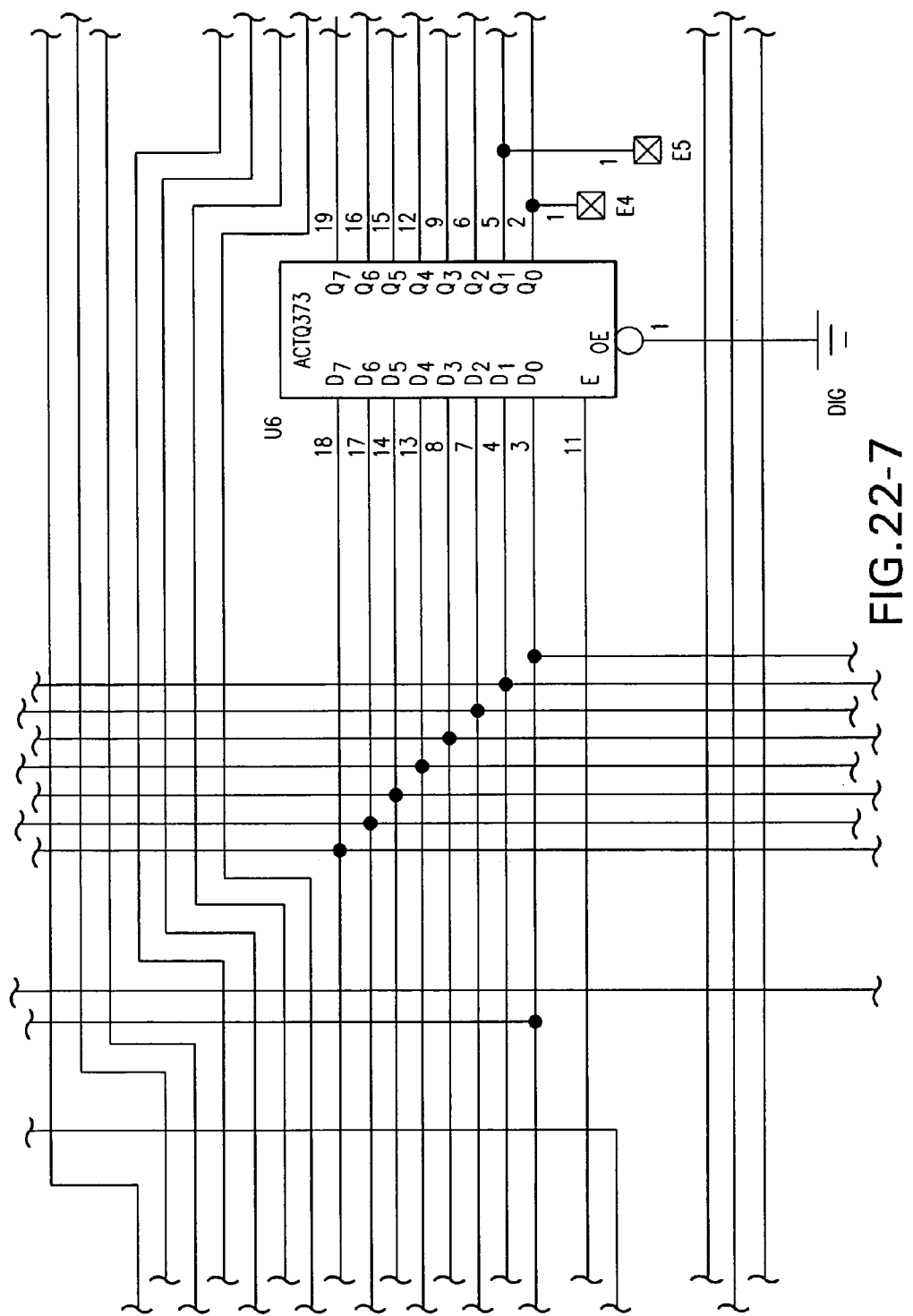
Figures 8, 22:
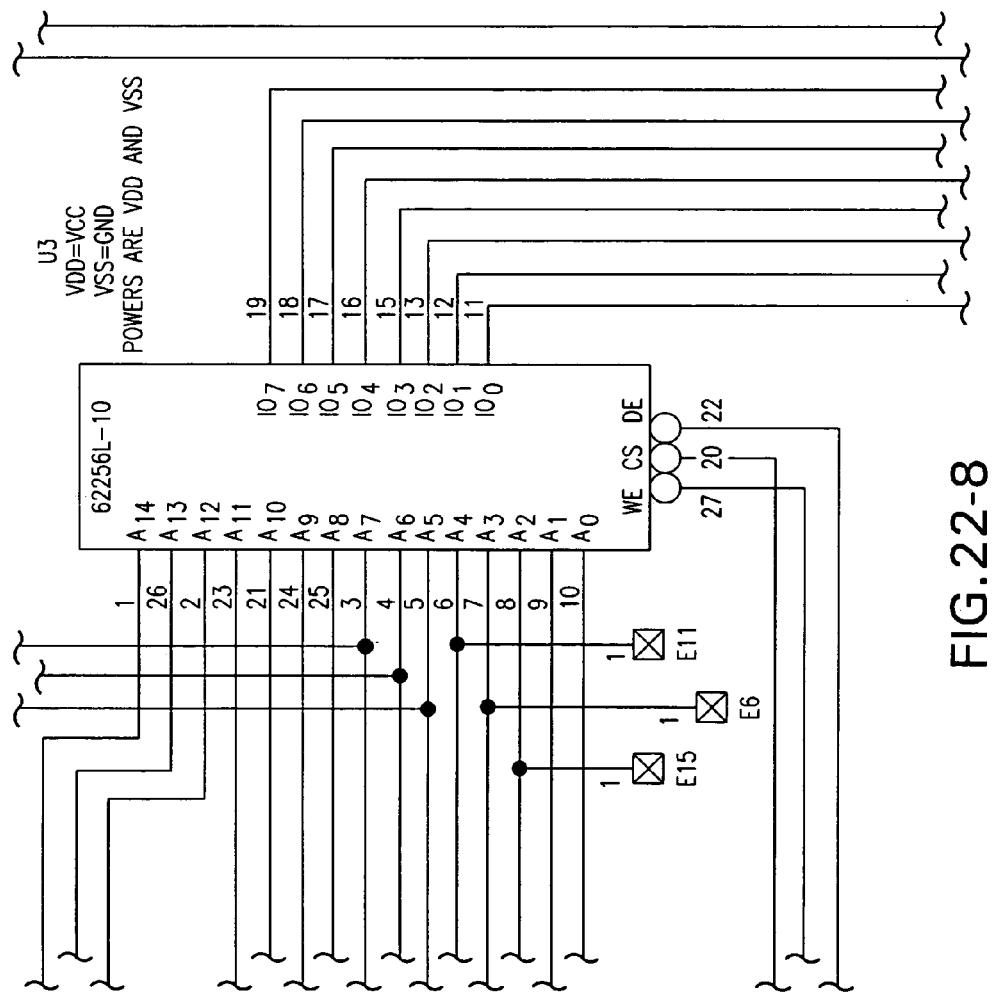
Figures 9, 22:
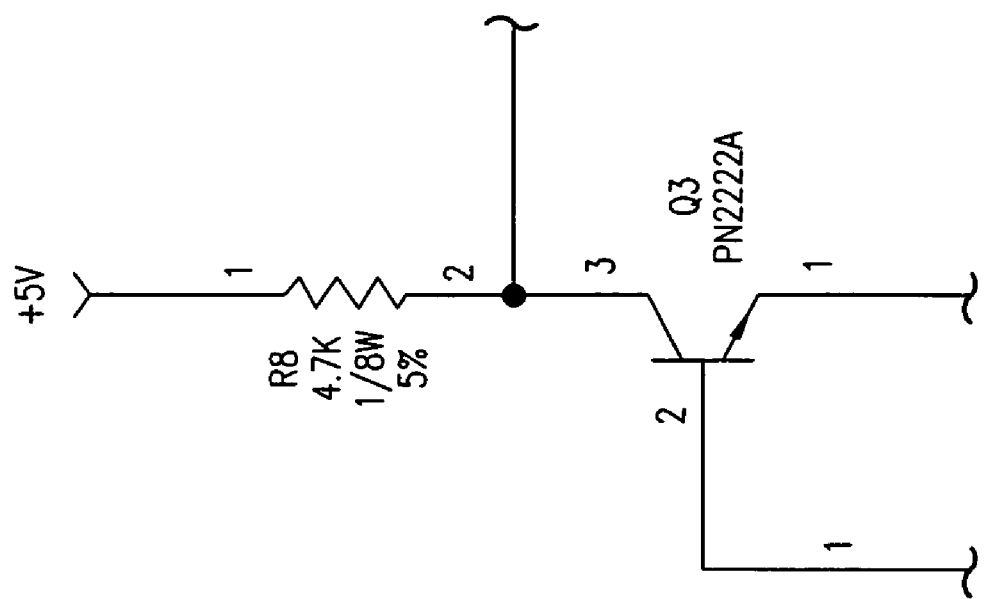
Figures 11, 22:
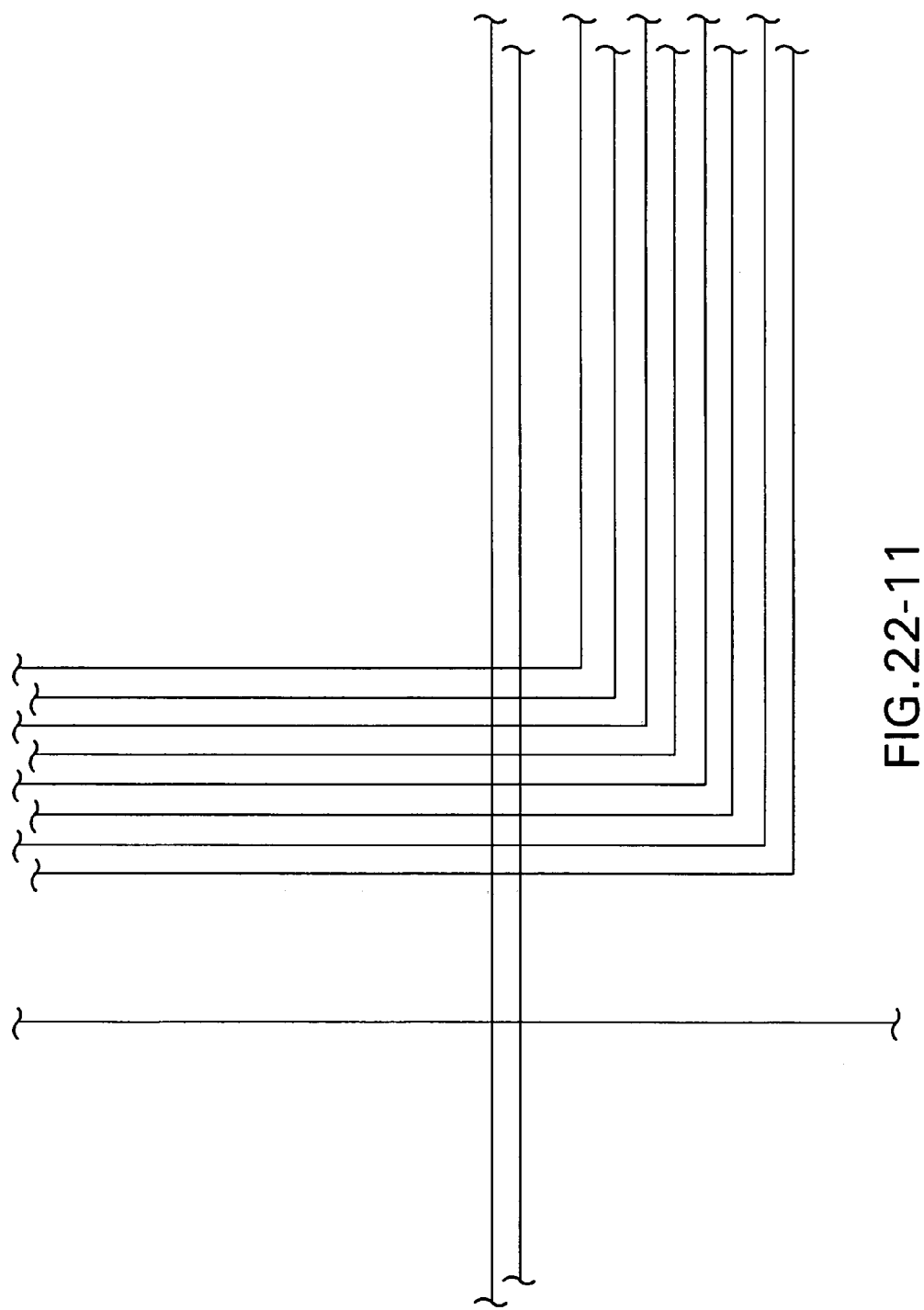
Figures 12, 22:
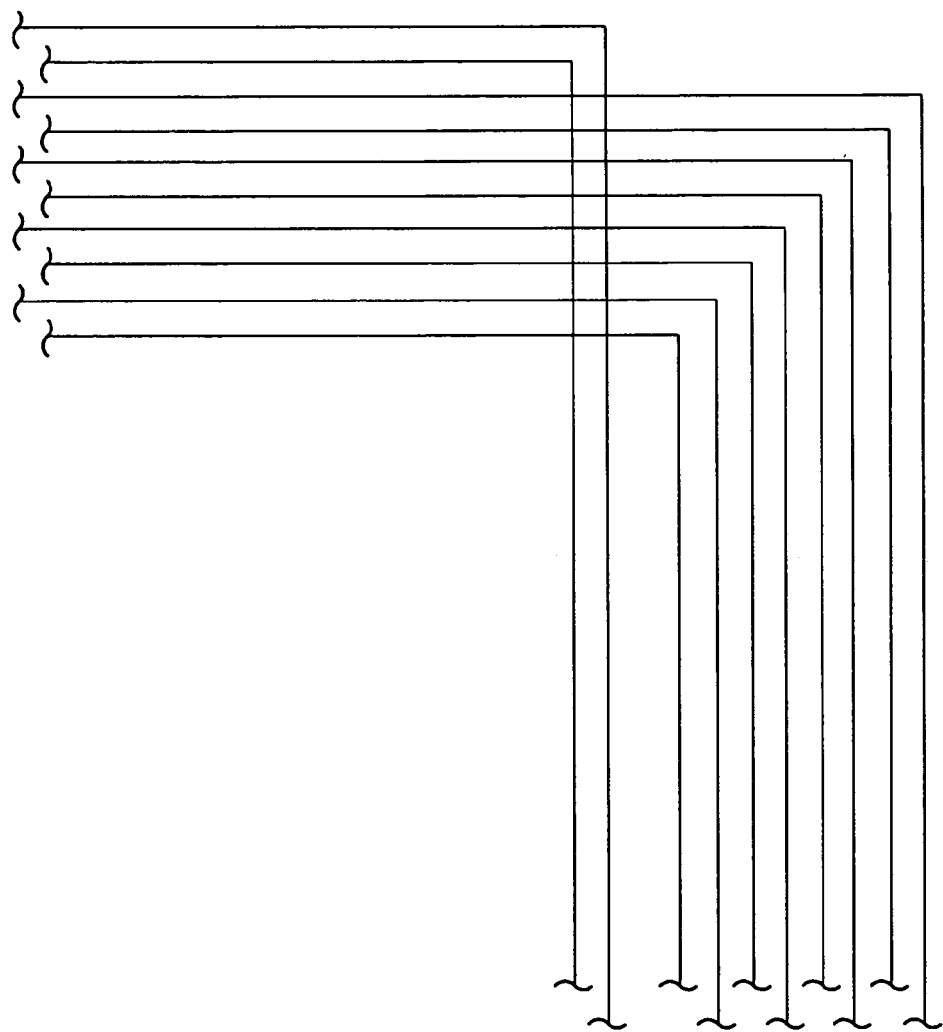
Figures 13, 22:
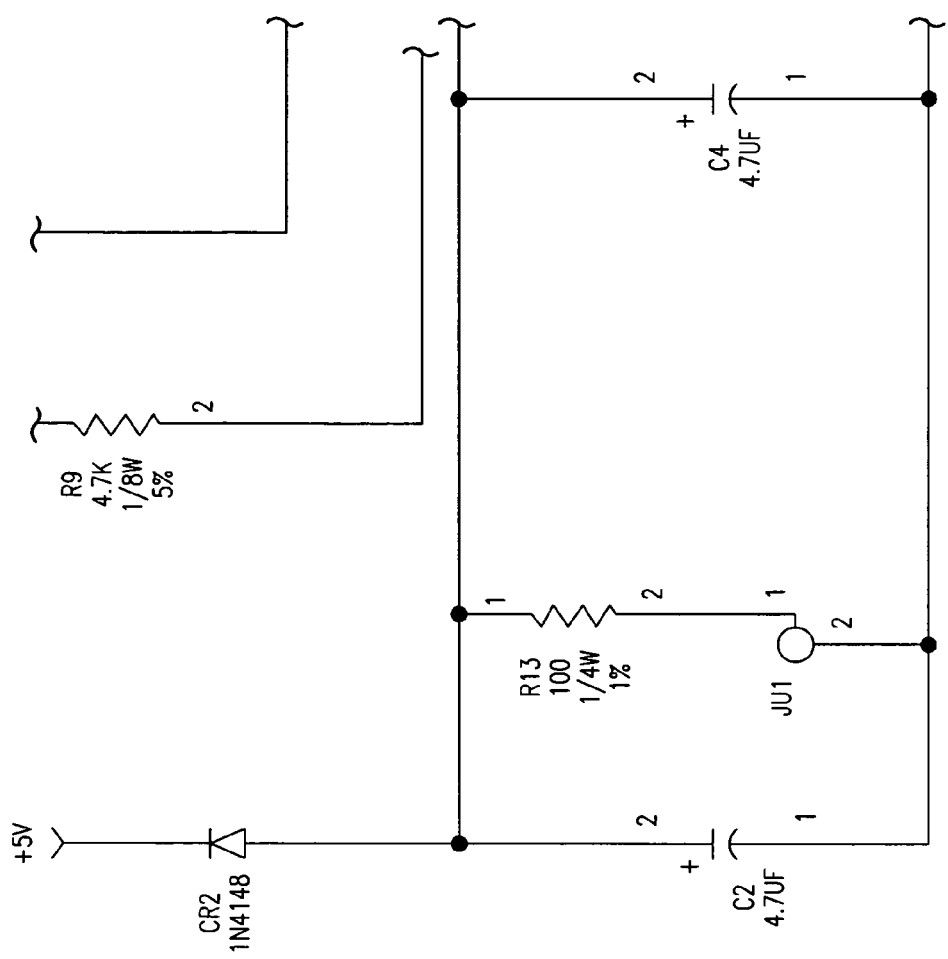
Figures 14, 22:
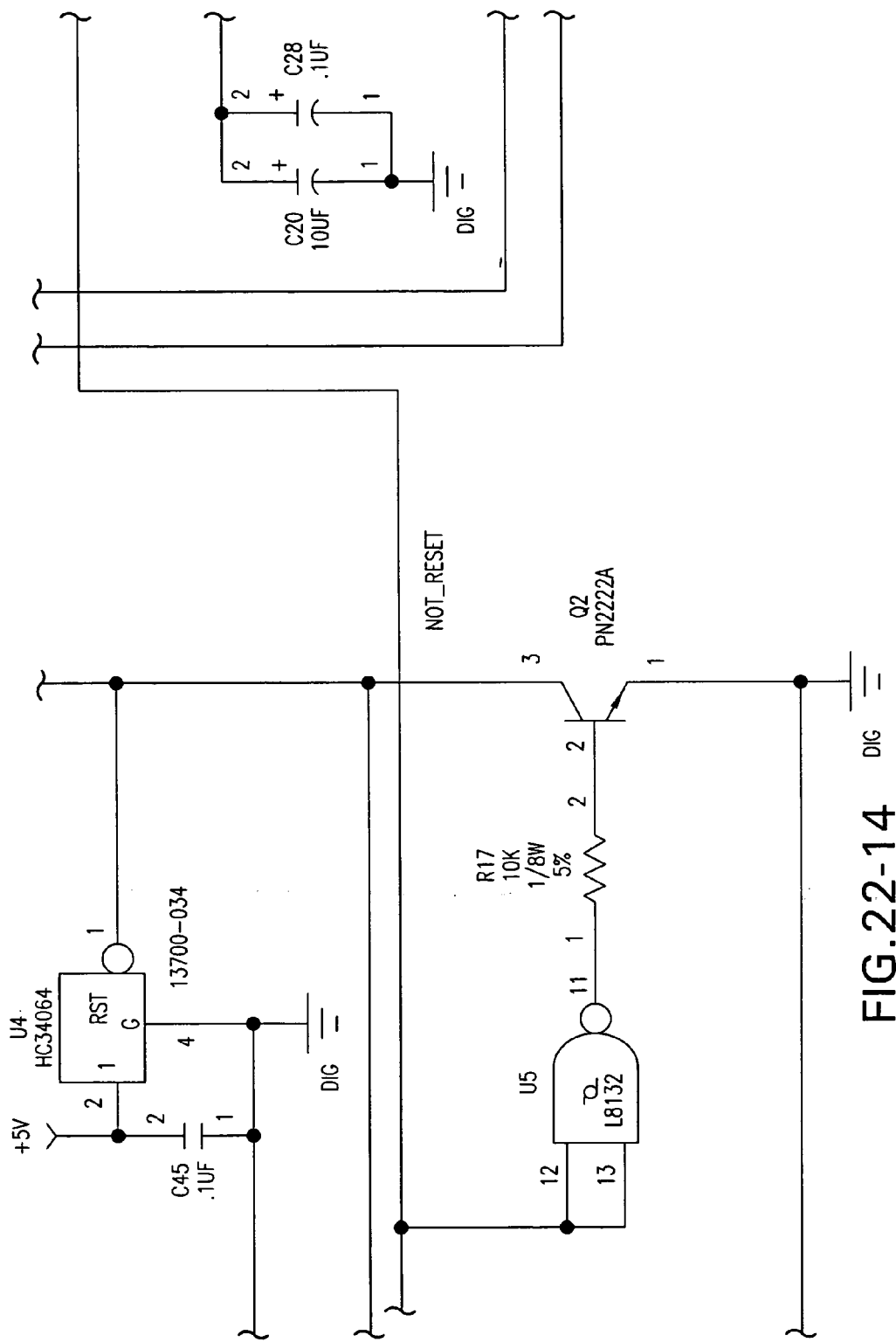
Figures 15, 22:
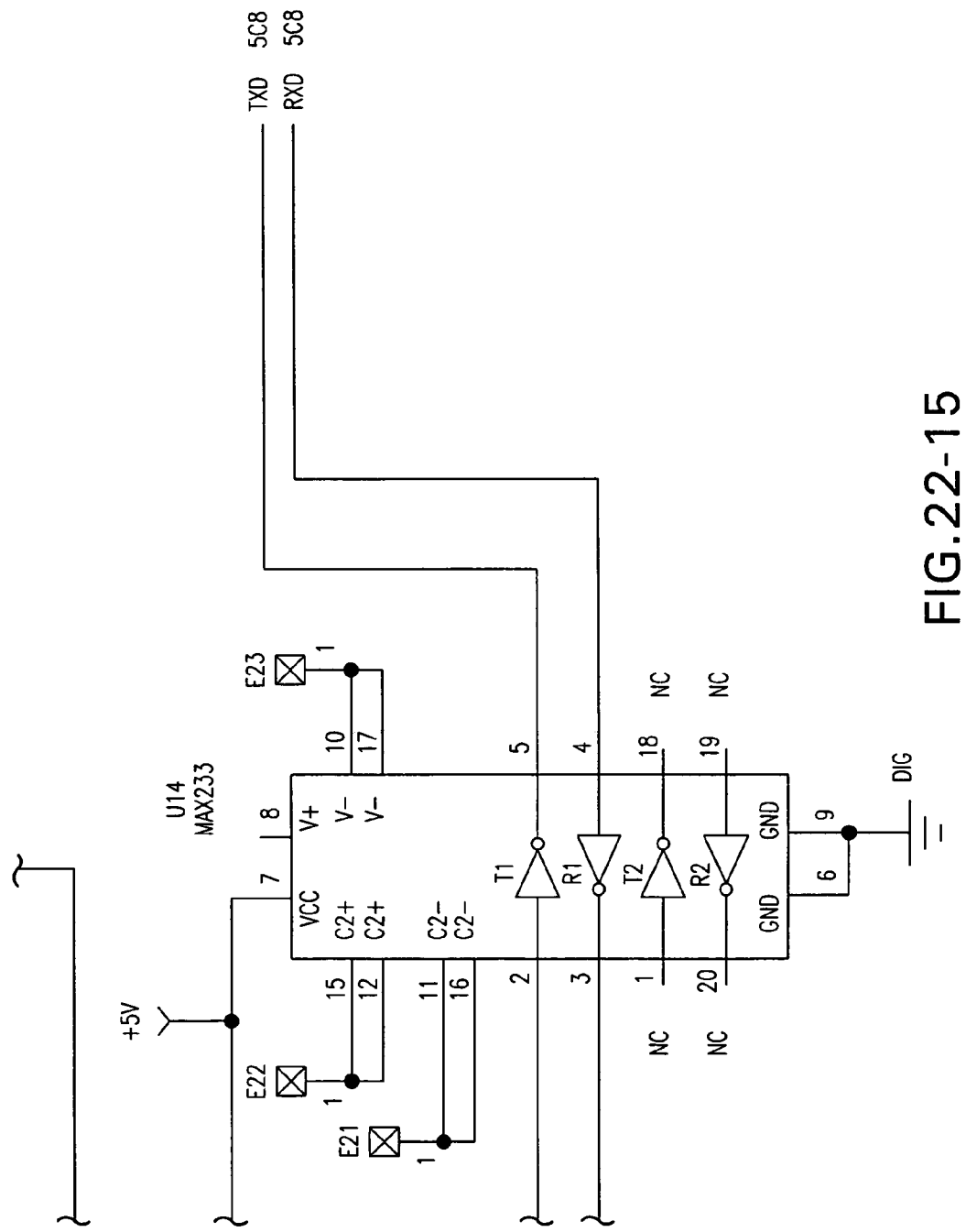
Figure 23:
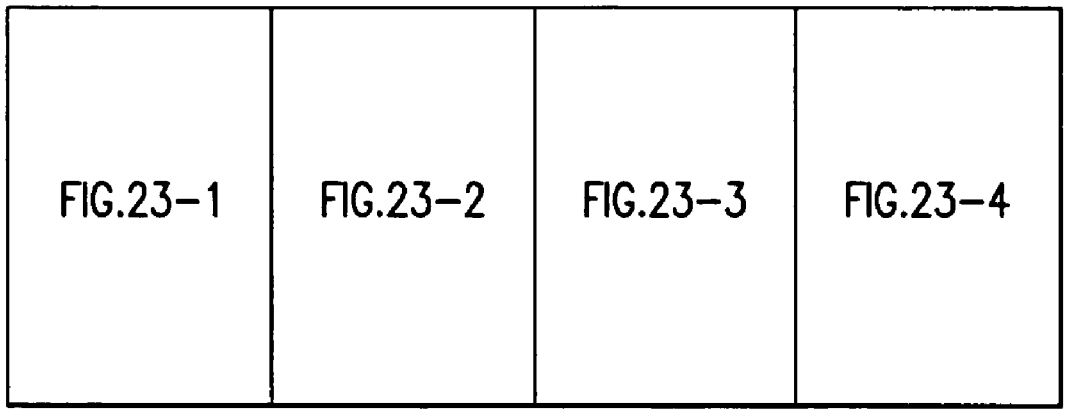
Figures 1, 23:
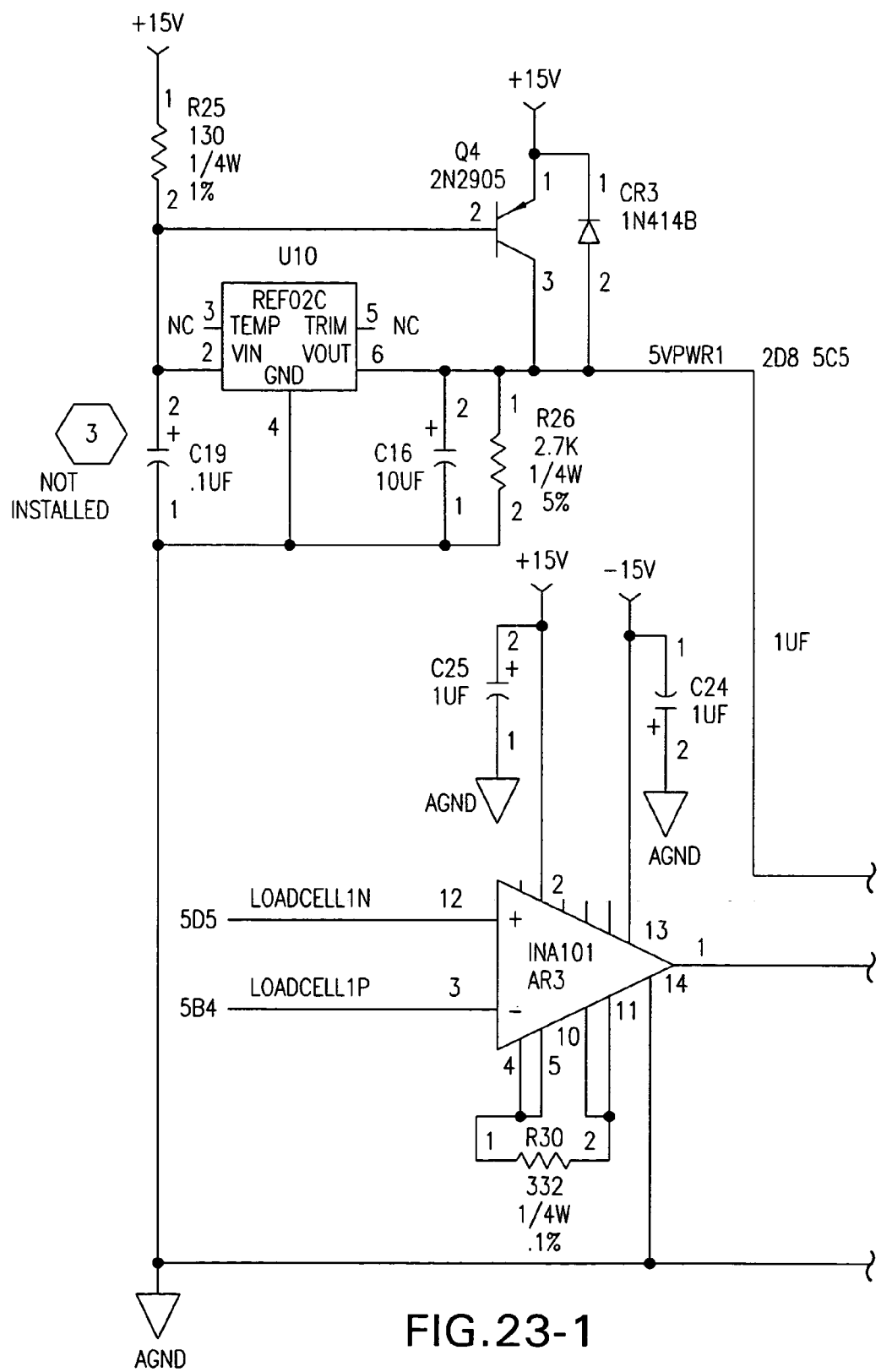
Figures 2, 23:
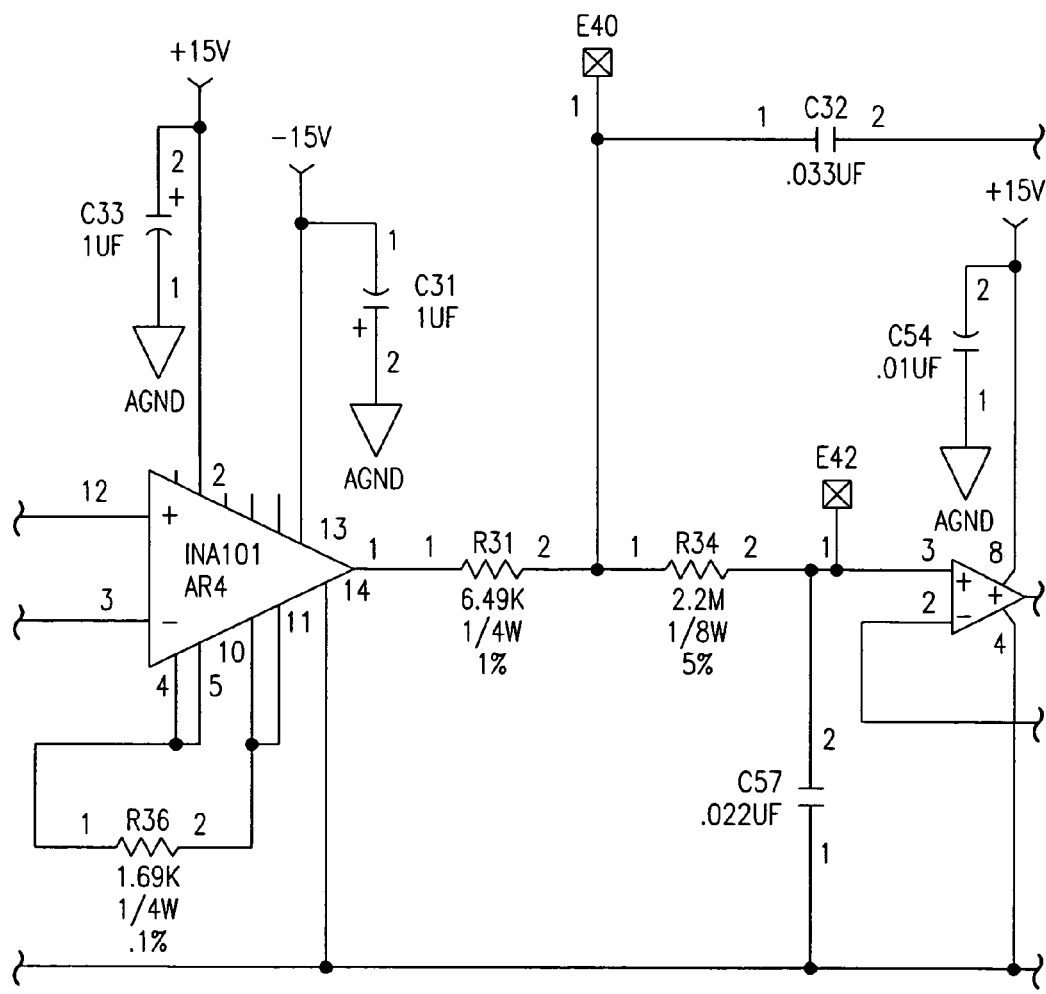
Figures 3, 23:
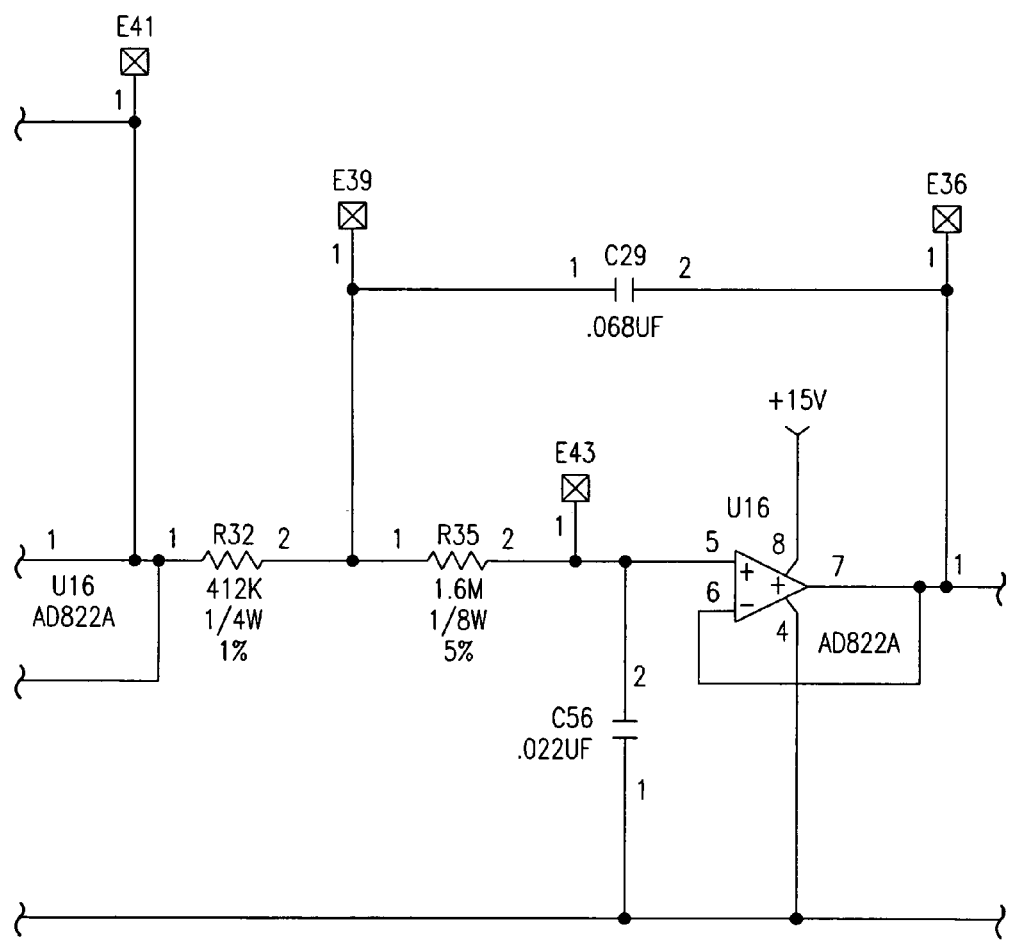
Figures 4, 23:
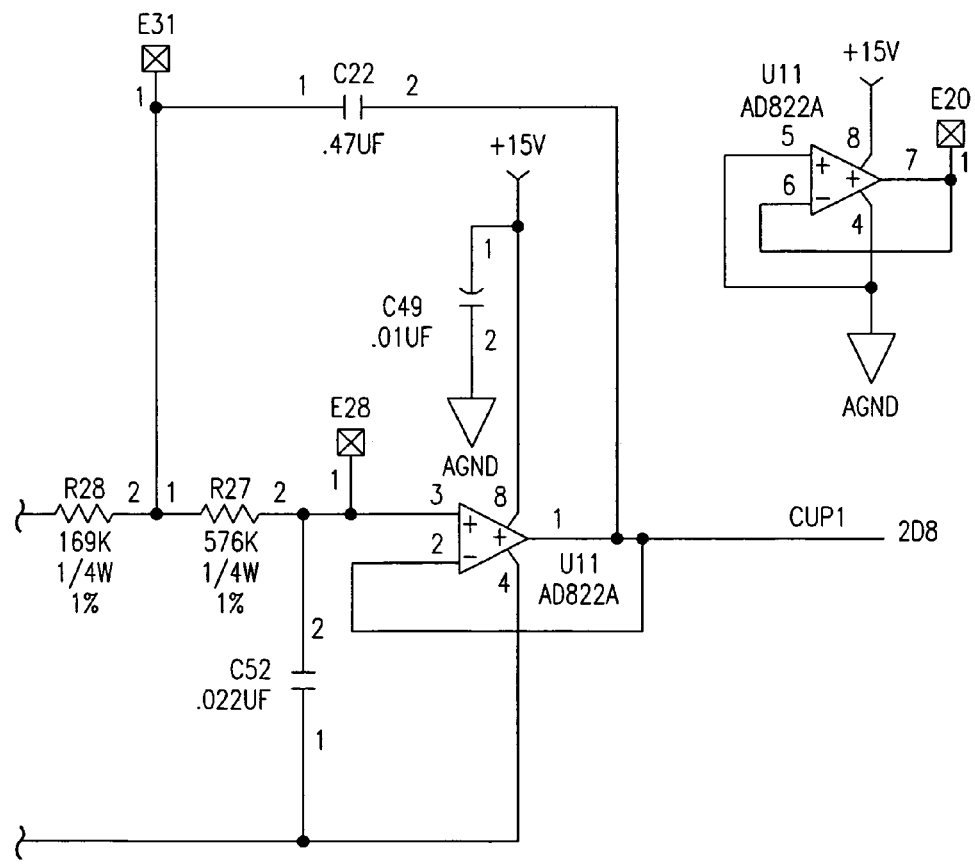
Figure 24:
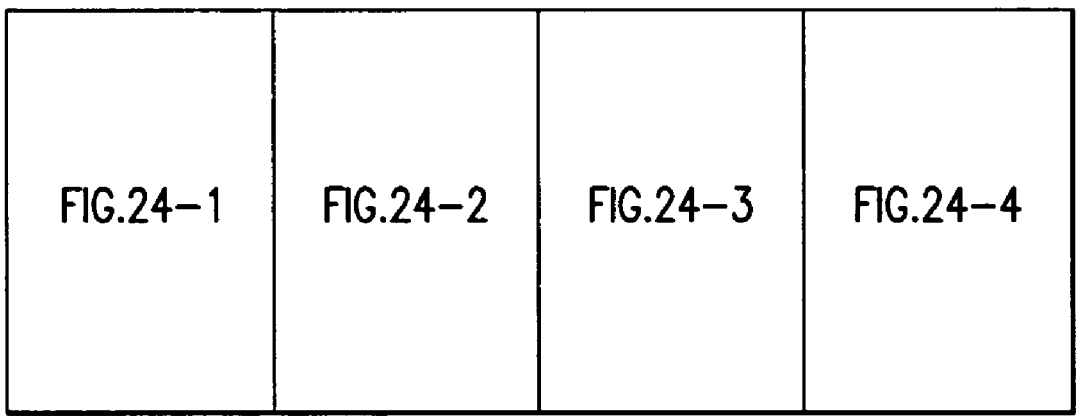
Figures 1, 24:
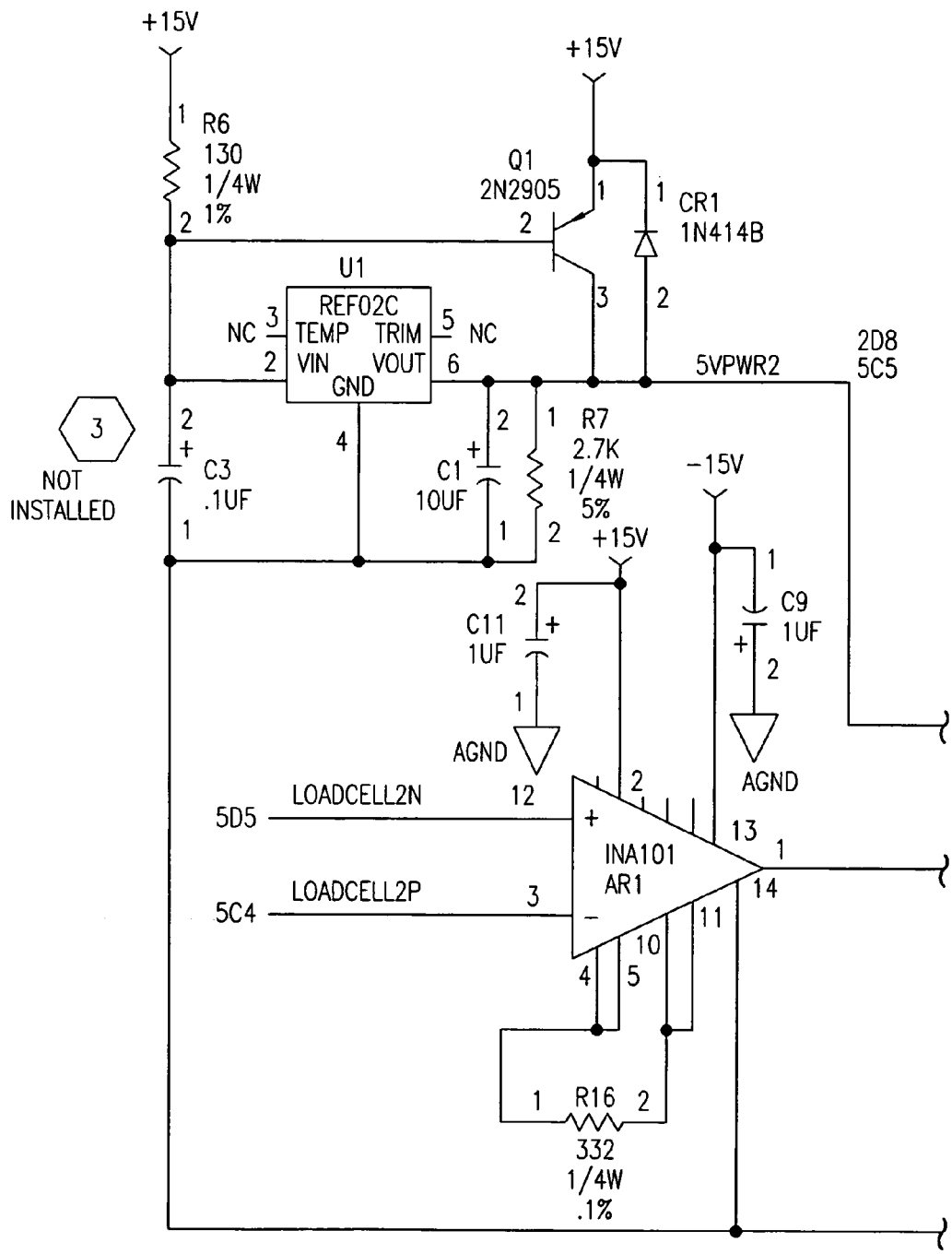
Figures 2, 24:
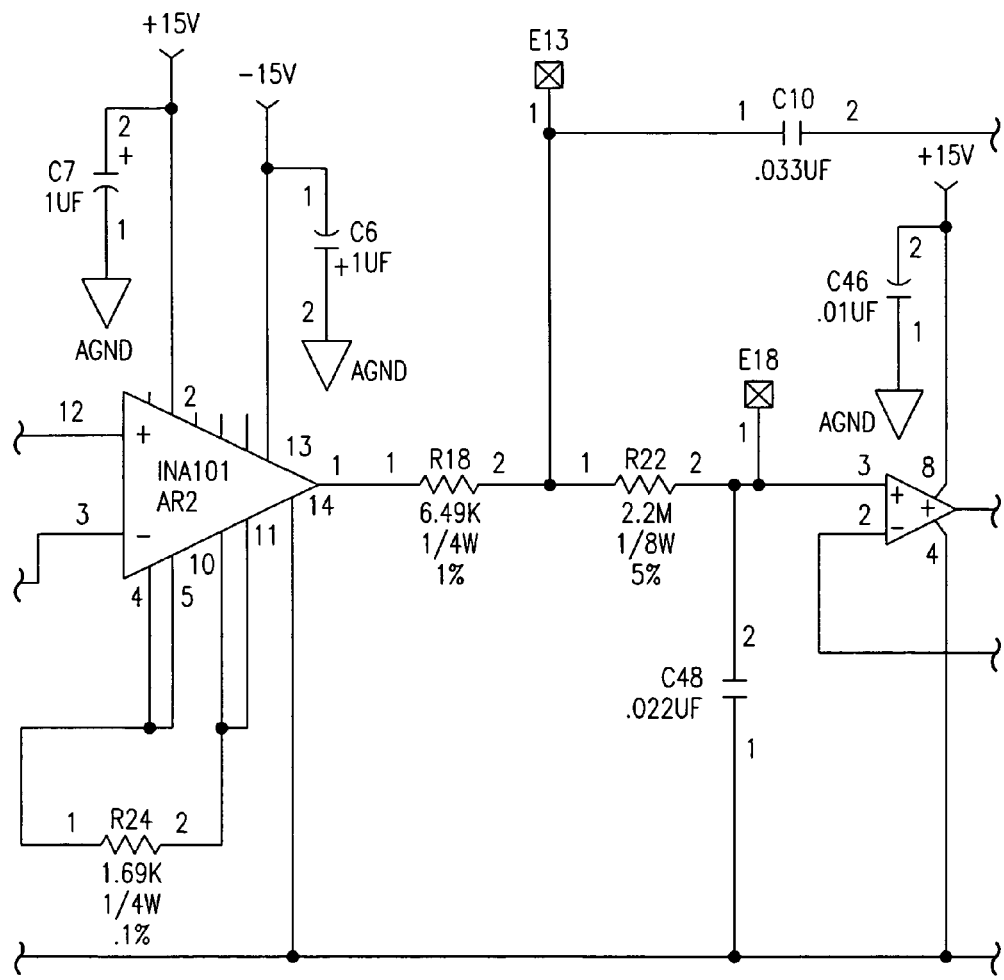
Figures 3, 24:
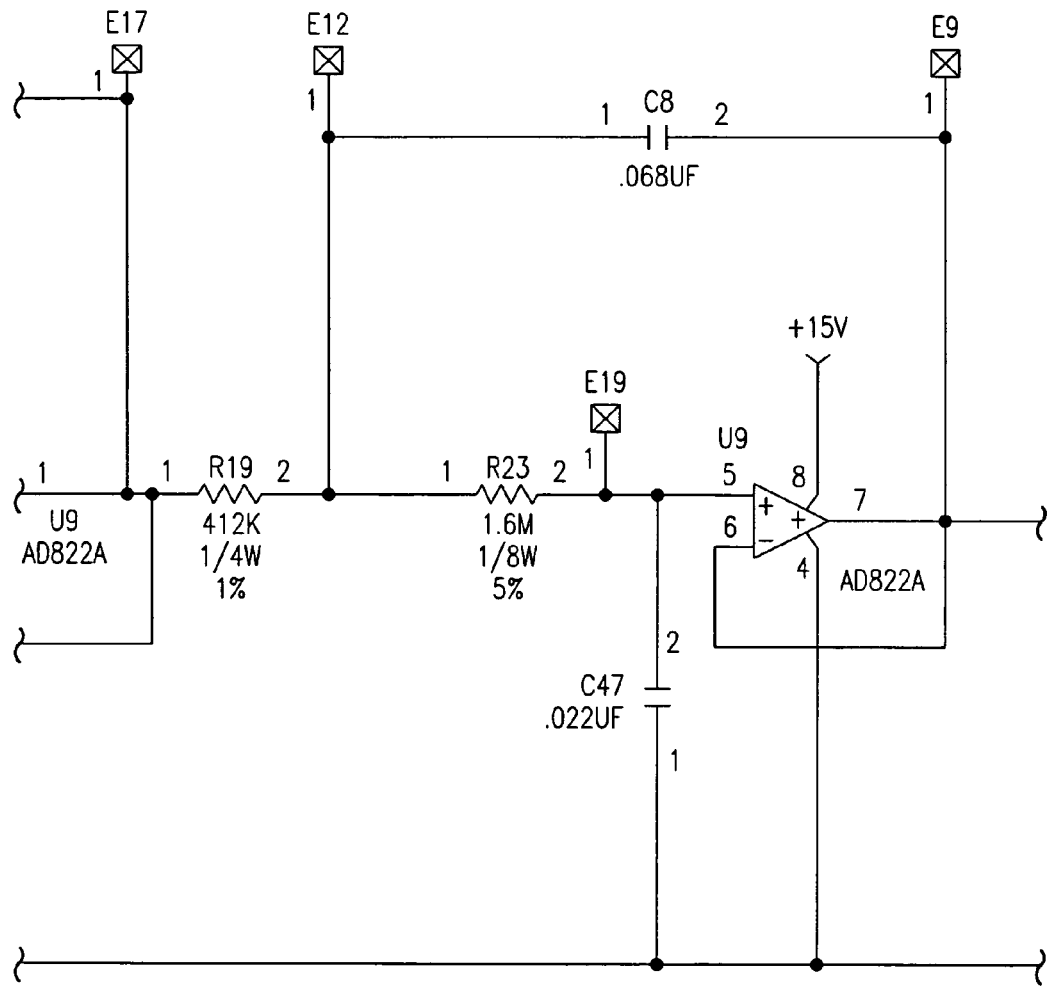
Figures 4, 24:
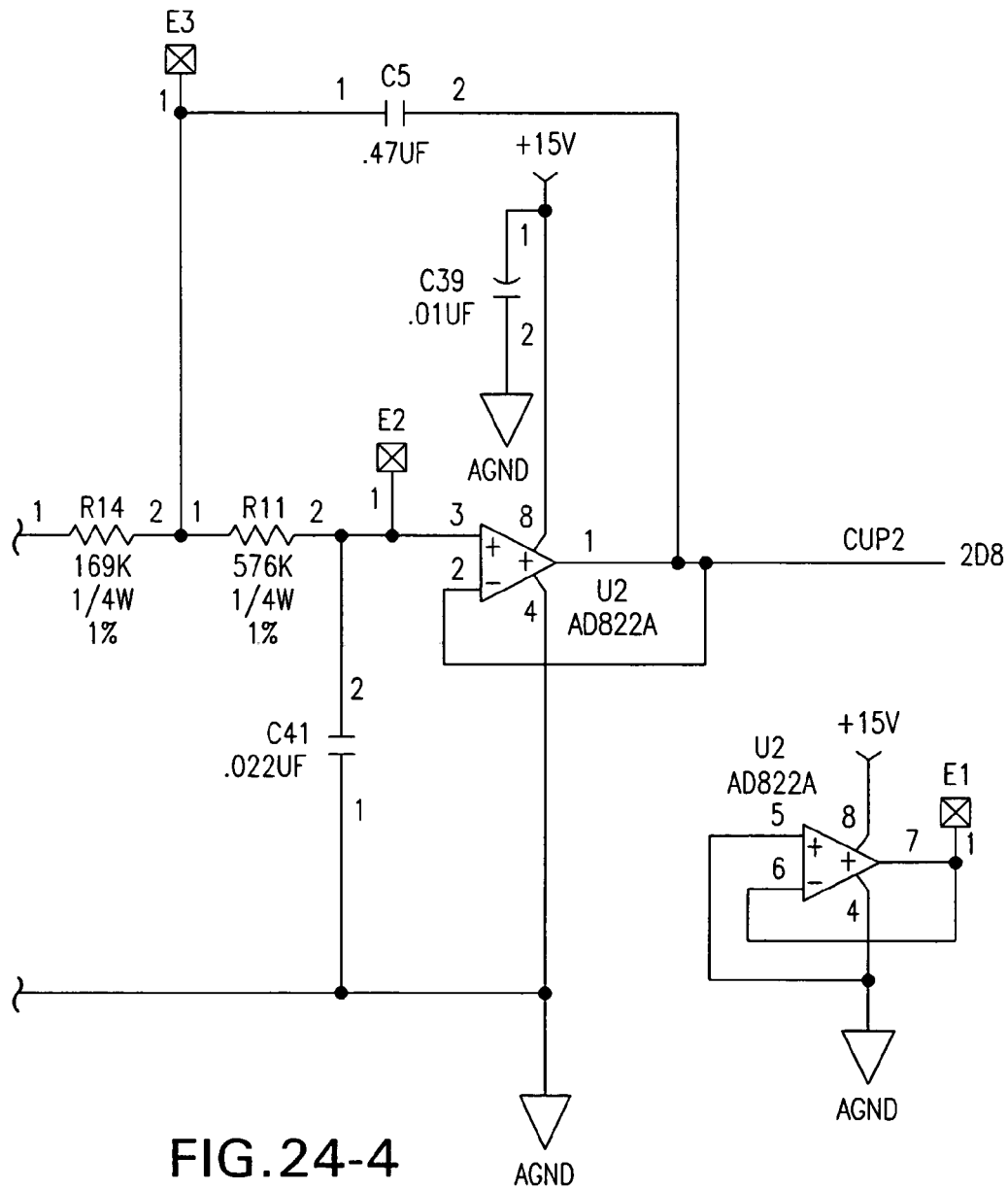
Figure 25:
Figure 1:
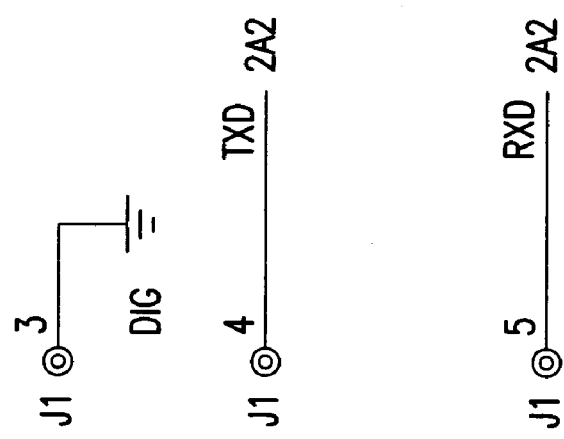
Figures 2, 25:
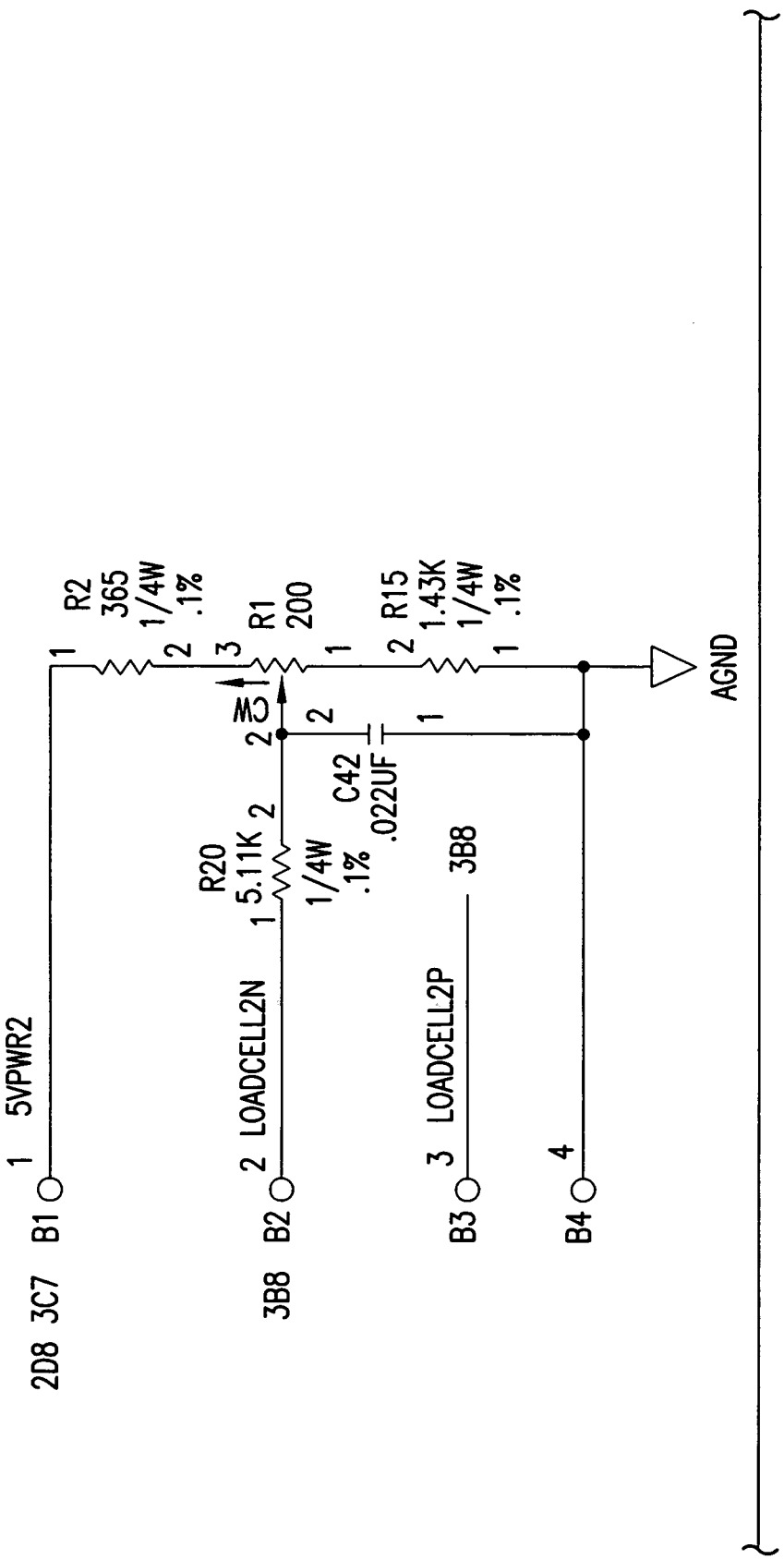
Figures 3, 25:
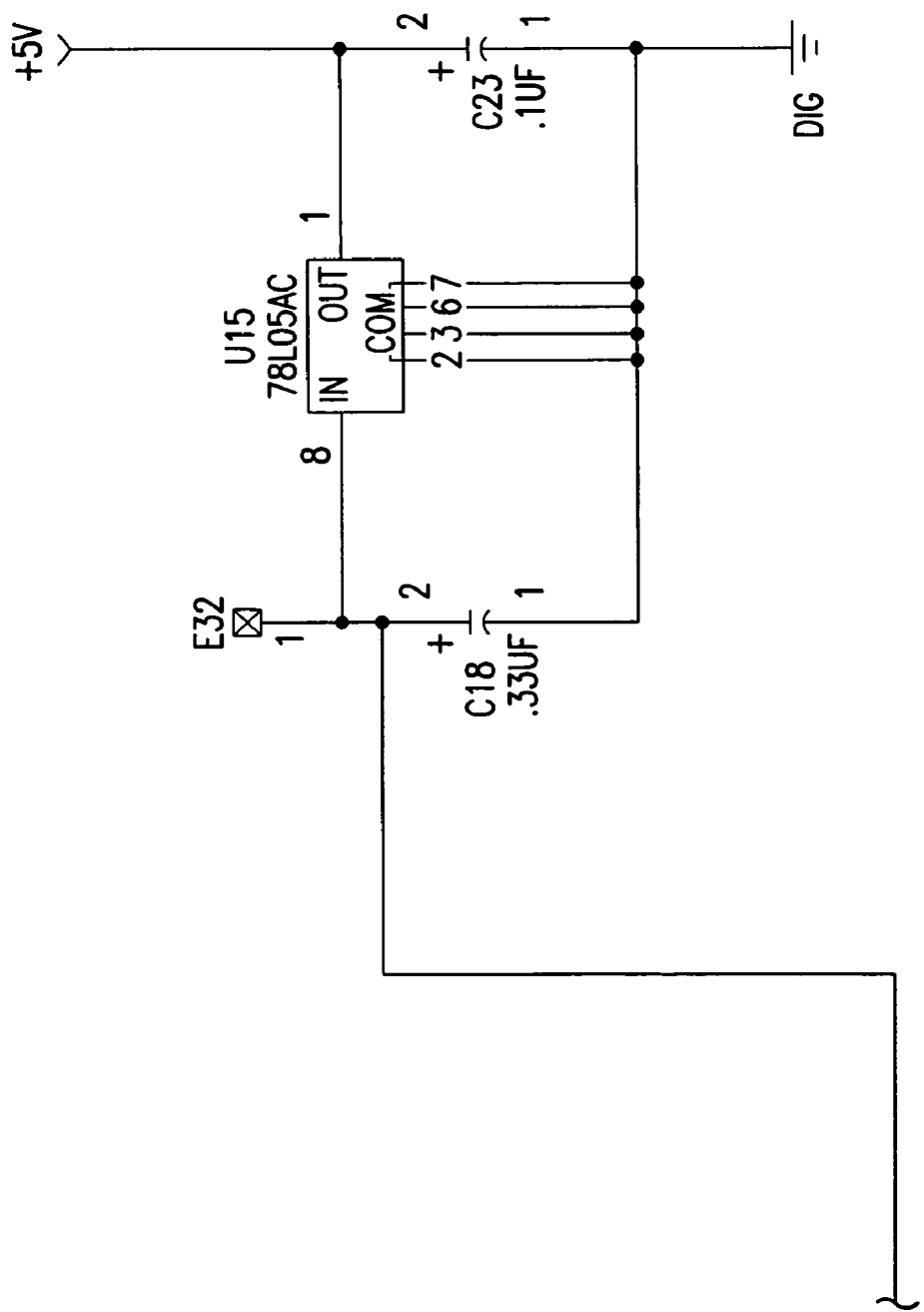
Figures 4, 25:
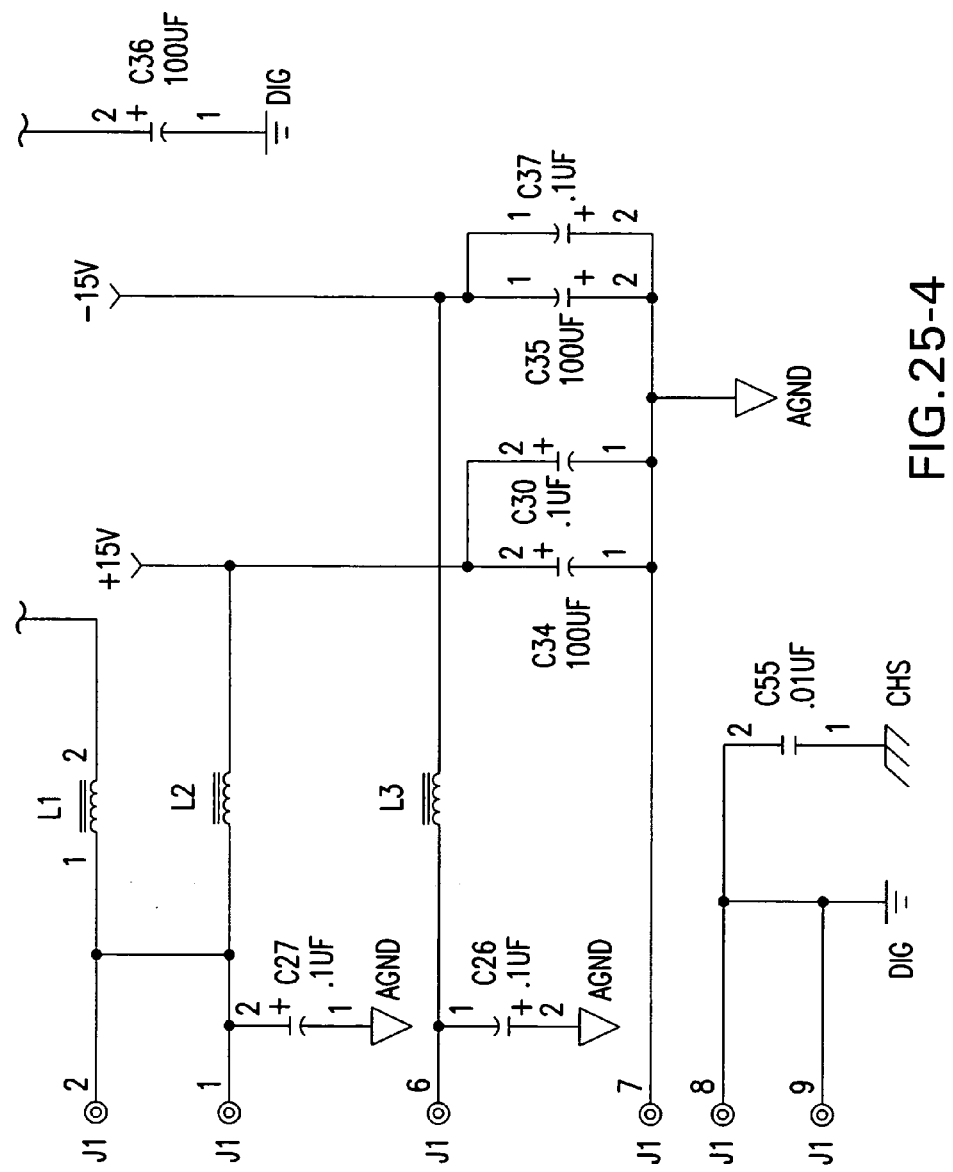
Figures 5, 25:
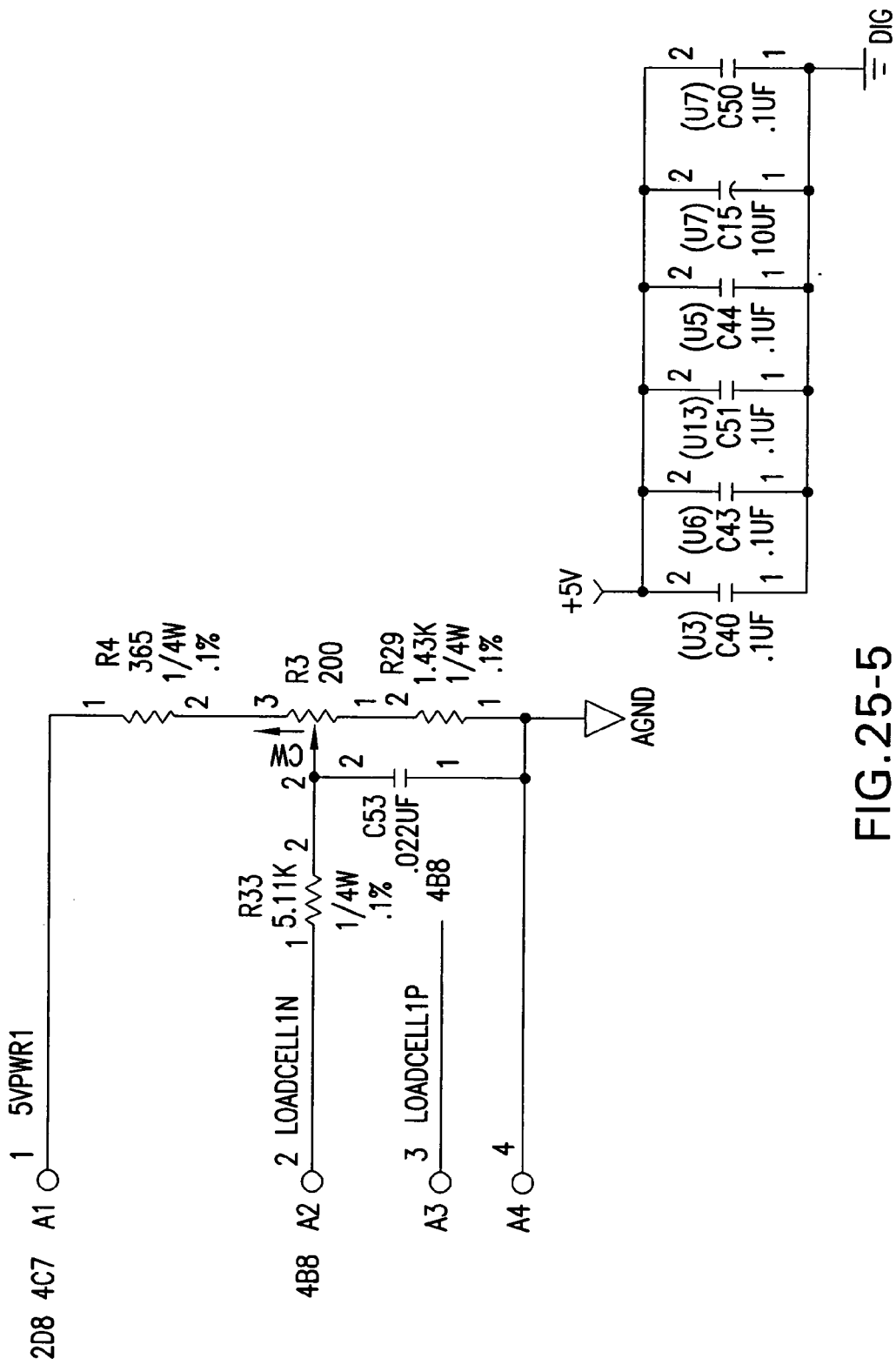

FIG. 22 is a schematic diagram of an embodiment of the digital electronics section of the electronic board of the apparatus of this invention. FIG. 23 is a schematic diagram of an embodiment of the A channel of the analog electronics section of the electronic board of the apparatus of this invention. FIG. 24 is a schematic diagram of an embodiment of the B channel of the analog electronics section of the electronic board of the apparatus of this invention. FIG. 25 is a schematic diagram of an embodiment of a balancing circuit for the A channel and the B channel of the apparatus of this invention. FIG. 25 also shows embodiments of a power filter and a power regulator. Table III lists the names of the parts shown in FIGS. 22, 23, 24, and 25.

TABLE III

| Name of component | Symbol in FIGS. 22, 23, 24, 25 |
| --- | --- |
| Assigned terminal | A |
| Analog device | AR |
| Assigned terminal | B |
| Capacitor | C |
| Electrolytic capacitor | ELCAP |
| Diode or rectifier | CR |
| LED signal device | DS |
| Probe point used by the test fixture of the PCB assembly | E |
| Connector | J |
| Jumper | JU |
| Inductor | L |
| Transistor | Q |
| Resistor | R |
| Test point | TP |
| Digital device | U |
| Oscillator | Y |

Port 0 of the microcontroller 118 is an 8-bit open drain bi-directional I/O port distributed from the microcontroller 118 to latches for the A/D converter 112 and the external random access memory (RAM). Port 0 is the multiplexed low-order address and data bus during accesses to external RAM. Port 0 is also the data bus for accesses to the latch on the A/D converter parallel output bus. Port 0 of the microcontroller 118 drives the lower address byte onto the parallel address bus for the external RAM, which is latched. The external RAM is preferably 32K×8 bit static RAM. Access time is less than 100 ns. External RAM is accessed in nonpage mode from the microcontroller 118.

Port 1 of the microcontroller 118 is an 8-bit bi-directional I/O port with internal pull-ups. P1(0) and P1(1) are used as the address lines to the A/D converter 112. P1(2) is used to control the Read/Convert input of the A/D converter 112. P1(3) is used to control the Byte select of the A/D converter 112.

Port 2 of the microcontroller 118 is an 8-bit bi-directional I/O port with internal pull-ups. Port 2 of the microcontroller 118 emits the high-order address byte during accesses to external RAM (16-bit addresses). Port 2 of the microcontroller 118 drives the upper address byte onto the parallel address bus for the external RAM, which is not latched externally to the microcontroller 118. P2 (7) is also used as a device select for the A/D converter 112.

Microcontroller interrupt INT0/ is driven by the A/D converter Busy signal while microcontroller interrupt INT1/ is disabled by pull-up to 5 VDC. A logic high on the microcontroller reset input for two machine cycles while the oscillator is running resets the microcontroller 118.

Two TTL compatible lines distributed from the microcontroller control I/O bus bits 0 and 1, P1(0) and P1(1), to the respective register address bits A(0) and A(1) of the A/D converter 112. These lines are used to select one of four channels to be converted.

Busy/falls when conversion is started and remains LOW until the conversion is completed and the data is latched into the output register. The output data will be valid when Busy/rises, so that the rising edge can be used to latch the data. The A/D converter Busy/ line drives the INT0/ input to the microcontroller 118.

The A/D converter byte select determines which byte is available on the A/D converter parallel data bus. Changing BYTE with CS/ LOW and R/C/ HIGH will cause the data bus to change accordingly. LOW selects the 8 MSBs. HIGH selects the 8 LSBs. This line is connected to P1(3) of the microcontroller 118.

A/D converter read/convert input, connected to P1(2) of the microcontroller 118, is used to control the initiation of the A/D converter read and convert cycle.

In the "ABBOTT PRISM" system, a curtain of gaseous fluid, preferably air, flows around the tips of the nozzles that dispense liquids in order to reduce splattering and accumulation of reagent on the exterior surfaces of the tips of the nozzles during the priming process. The apparatus of this invention can be used as a diagnostic tool to detect the presence and relative magnitude of the flow of gaseous fluid during routine maintenance so that the tips of the nozzles experiencing insufficient flow of gaseous fluid can be identified and adjusted. The method of detection of the volumetric rate of flow of gaseous fluid involves allowing the stream of gaseous fluid to impinge on the bottom of the weigh cup of the apparatus of this invention, thereby creating a net force on the weigh cup, which can be detected by the load cell with which the weigh cup is associated. The force F acting on the weigh cup can be expressed, approximately, as $$F=kq^2$$

where k is a constant and q represents the volumetric rate of flow of air or other gaseous fluid.

The same apparatus and procedures as were used to detect the volumes of liquid dispensed can be used to detect and measure the force F and the volumetric rate of flow q of air or other gaseous fluid. The term k is dependent upon the density of the fluid whose rate of flow is being measured.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method of calibrating an apparatus for determining the volume of liquid dispensed by a liquid-dispensing mechanism of an analytical instrument, said method comprising the steps of:
   (a) providing said apparatus, said apparatus comprising:
      (1) at least one weigh cup;
      (2) at least one standard mass;
      (3) at least one transducer assembly to convert a value of weight to an electrical response; and
      (4) at least one electronic circuit for converting said electrical response to a measurement of volume of liquid dispensed;
   (b) recording the value of weight of one of said at least one weigh cup and one of said at least one standard mass when said one of said at least one standard mass is in said one of said at least one weigh cup;
   (c) recording the value of weight of said one of said at least one weigh cup when said one of said at least one weigh cup is empty; and
   (d) calibrating the apparatus by computing the gain based on the response of the electronic circuit.

2. The method of claim 1, further including the step of compensating for the drift of the at least one transducer assembly.

3. The method of claim 1, wherein a gain of at least 1.2 Volts/gram is obtained.

4. A method of calibrating an apparatus for determining the volume of gaseous fluid dispensed in the vicinity of a liquid-dispensing mechanism of an analytical instrument, said method comprising the steps of:
   (a) providing said apparatus, said apparatus comprising:
      (1) at least one weigh cup;
      (2) at least one standard mass;
      (3) at least one transducer assembly to convert a value of weight to an electrical response; and
      (4) at least one electronic circuit for converting said electrical response to a measurement of volume of liquid dispensed;
   (b) recording the value of weight of one of said at least one weigh cup and one of said at least one standard mass when said one of said at least one standard mass is in said one of said at least one weigh cup;
   (c) recording the value of weight of said one of said at least one weigh cup when said one of said at least one weigh cup is empty; and (d) calibrating the apparatus by computing the gain based on the response of the electronic circuit.

* * * * *